United States Patent
Plumptre

(10) Patent No.: US 9,345,840 B2
(45) Date of Patent: May 24, 2016

(54) DRUG DELIVERY DOSE SETTING MECHANISM WITH VARIABLE MAXIMUM DOSE

(75) Inventor: David Aubrey Plumptre, Worcestershire (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 641 days.

(21) Appl. No.: 12/788,665

(22) Filed: May 27, 2010

(65) Prior Publication Data

US 2010/0324527 A1 Dec. 23, 2010

Related U.S. Application Data

(60) Provisional application No. 61/182,816, filed on Jun. 1, 2009.

(30) Foreign Application Priority Data

Jul. 10, 2009 (EP) .................................. 09009055

(51) Int. Cl.
*A61M 5/00* (2006.01)
*A61M 5/315* (2006.01)

(52) U.S. Cl.
CPC ... *A61M 5/31536* (2013.01); *A61M 2005/3154* (2013.01)

(58) Field of Classification Search
CPC .............. A61M 5/31; A61M 5/31536; A61M 2005/3154; A61M 5/31533; A61M 5/31535; A61M 5/3148; A61M 5/31528; A61M 5/31565; A61M 5/31593; A61M 5/31525
USPC ................................... 604/207–211, 187, 136
See application file for complete search history.

(56) References Cited

U.S. PATENT DOCUMENTS

| | | | |
|---|---|---|---|
| 3,302,462 A | | 2/1967 | Pursell |
| 5,226,895 A | * | 7/1993 | Harris ........................... 604/208 |
| 5,423,752 A | | 6/1995 | Haber et al. |
| 5,514,097 A | * | 5/1996 | Knauer ......................... 604/136 |
| 5,584,815 A | * | 12/1996 | Pawelka et al. ............... 604/191 |

(Continued)

FOREIGN PATENT DOCUMENTS

| | | |
|---|---|---|
| DE | 93 01 334 U1 | 4/1993 |
| DE | 197 30 999 C1 | 12/1998 |

(Continued)

OTHER PUBLICATIONS

Machine Deisgn, Penton Media, vol. 65, No. 11 (1993) p. 36 "Standard Compression Springs Save Space".

*Primary Examiner* — Bhisma Mehta
*Assistant Examiner* — Bradley G Thomas, Jr.
(74) *Attorney, Agent, or Firm* — McDonnell Boehnen Hulbert & Berghoff LLP

(57) ABSTRACT

A method and system for proving a drug delivery device having a variable dose. The drug delivery device comprising a first tubular member and a second tubular member rotatably coupled to the first tubular member. A maximum stop component is operatively coupled to the first and second tubular member such that the maximum stop component is movable from a first position to a second position. The first position defines a first maximum dose that may be set by a user of said drug delivery device and the second position defines a second maximum dose that may be set by the user of said drug delivery device.

12 Claims, 19 Drawing Sheets

(56) References Cited

U.S. PATENT DOCUMENTS

| | | | | |
|---|---|---|---|---|
| 5,591,136 | A | * | 1/1997 | Gabriel .................. 604/211 |
| 5,593,390 | A | * | 1/1997 | Castellano et al. ........... 604/187 |
| 5,792,117 | A | | 8/1998 | Brown |
| 5,820,602 | A | | 10/1998 | Kovelman et al. |
| 6,090,080 | A | | 7/2000 | Jost et al. |
| 6,936,032 | B1 | | 8/2005 | Bush, Jr. et al. |
| 7,811,263 | B2 | * | 10/2010 | Burren et al. ................. 604/211 |
| RE41,956 | E | * | 11/2010 | Klitgaard et al. .............. 604/181 |
| 2003/0050609 | A1 | * | 3/2003 | Sams ........................... 604/208 |
| 2004/0127858 | A1 | | 7/2004 | Bendek et al. |
| 2004/0162528 | A1 | | 8/2004 | Horvath et al. |
| 2004/0186437 | A1 | | 9/2004 | Frenette et al. |
| 2004/0210199 | A1 | | 10/2004 | Atterbury et al. |
| 2004/0236285 | A1 | | 11/2004 | Fisher et al. |
| 2005/0137571 | A1 | | 6/2005 | Hommann |
| 2006/0153693 | A1 | | 7/2006 | Fiechter et al. |
| 2006/0258988 | A1 | | 11/2006 | Keitel et al. |
| 2007/0021718 | A1 | | 1/2007 | Burren et al. |
| 2008/0027397 | A1 | | 1/2008 | DeRuntz et al. |
| 2008/0077095 | A1 | | 3/2008 | Kirchhofer |
| 2008/0183139 | A1 | * | 7/2008 | Burren et al. ................. 604/211 |
| 2008/0208123 | A1 | | 8/2008 | Hommann |
| 2009/0227959 | A1 | | 9/2009 | Hirschel et al. |

FOREIGN PATENT DOCUMENTS

| | | |
|---|---|---|
| DE | 298 18 721 U1 | 3/2000 |
| DE | 10 2005 063 311 A1 | 8/2006 |
| DE | 10 2005 060 928 A1 | 6/2007 |
| DE | 10 2006 038 123 A1 | 2/2008 |
| DE | 10 2007 026 083 A1 | 11/2008 |
| EP | 0 897 728 A1 | 2/1999 |
| EP | 0 937 471 A2 | 8/1999 |
| EP | 0 937 472 A2 | 8/1999 |
| EP | 1 541 185 A1 | 6/2005 |
| EP | 1 776 975 A2 | 4/2007 |
| EP | 1 923 084 A1 | 5/2008 |
| GB | 2 443 390 A | 5/2008 |
| WO | 92/18180 A1 | 10/1992 |
| WO | 93/07922 A1 | 4/1993 |
| WO | 96/23973 A1 | 8/1996 |
| WO | 96/39214 A1 | 12/1996 |
| WO | 97/10864 A1 | 3/1997 |
| WO | 99/03520 A1 | 1/1999 |
| WO | 01/19434 A1 | 3/2001 |
| WO | 03/080160 A1 | 10/2003 |
| WO | 2004/020028 A1 | 3/2004 |
| WO | 2004/064902 A1 | 8/2004 |
| WO | 2004/078241 A1 | 9/2004 |
| WO | 2004/078242 A2 | 9/2004 |
| WO | 2004/078293 A1 | 9/2004 |
| WO | 2005/018721 A1 | 3/2005 |
| WO | 2005/021072 A1 | 3/2005 |
| WO | 2005/044346 A2 | 5/2005 |
| WO | 2005/123159 A2 | 12/2005 |
| WO | 2006/024461 A1 | 3/2006 |
| WO | 2006/058883 A1 | 6/2006 |
| WO | 2006/079481 A2 | 8/2006 |
| WO | 2006/089767 A1 | 8/2006 |
| WO | 2006/114395 A1 | 11/2006 |
| WO | 2006/125328 A1 | 11/2006 |
| WO | 2007/017052 A1 | 2/2007 |
| WO | 2007/067889 A1 | 6/2007 |
| WO | 2008/031235 A1 | 3/2008 |
| WO | 2008/074897 A1 | 6/2008 |
| WO | 2008/116766 A1 | 10/2008 |
| WO | 2008/128373 A1 | 10/2008 |

* cited by examiner

DRUG DELIVERY DOSE SETTING MECHANISM WITH VARIABLE MAXIMUM DOSE

FIELD OF THE PRESENT PATENT APPLICATION

The present application is generally directed to dose setting mechanisms for drug delivery devices. More particularly, the present application is generally directed to dose setting mechanisms comprising a variable maximum dose. Aspects of the invention may be equally applicable in other scenarios as well.

BACKGROUND

Pen type drug delivery devices have application where regular injection by persons without formal medical training occurs. This may be increasingly common among patients having diabetes where self-treatment enables such patients to conduct effective management of their disease.

There are basically two types of pen type delivery devices that allow a user set to a variable dose of medication: resettable devices (i.e., reusable) and non-resettable (i.e., disposable). These types of pen delivery devices (so named because they often resemble an enlarged fountain pen) are generally comprised of three primary elements: (i) a cartridge section that includes a cartridge often contained within a housing or holder; (ii) a needle assembly connected to one end of the cartridge section; and (iii) a dosing section connected to the other end of the cartridge section. A cartridge (often referred to as an ampoule) typically includes a reservoir that is filled with a medication (e.g., insulin), a movable rubber type bung or stopper located at one end of the cartridge reservoir, and a top having a pierceable rubber seal located at the other, often necked-down, end. A crimped annular metal band is typically used to hold the rubber seal in place. While the cartridge housing may be typically made of plastic, cartridge reservoirs have historically been made of glass.

The needle assembly is typically a replaceable double-ended needle assembly. Before an injection, a replaceable double-ended needle assembly is attached to one end of the cartridge assembly, a dose is set, and then a dose is administered. Such removable needle assemblies may be threaded onto, or pushed (i.e., snapped) onto the pierceable seal end of the cartridge assembly.

The dosing section or dose setting mechanism is typically the portion of the pen device that is used to set a dose. During an injection, a spindle contained within the dose setting mechanism presses against the bung or stopper of the cartridge. This force causes the medication contained within the cartridge to be injected through an attached needle assembly. After an injection, as generally recommended by most drug delivery device and/or needle assembly manufacturers and suppliers, the needle assembly is removed and discarded.

Different types of pen delivery devices, including disposable (i.e., non-resettable) and reusable (i.e., resettable) varieties, have evolved over the years. For example, disposable pen delivery devices are supplied as self-contained devices. Such self-contained devices do not have removable pre-filled cartridges. Rather, the pre-filled cartridges may not be removed and replaced from these devices without destroying the device itself. Consequently, such disposable devices need not have a resettable dose setting mechanism.

In contrast to typical disposable pen type devices, typical reusable pen delivery devices feature essentially two main reusable components: a cartridge holder and a dose setting mechanism. After a cartridge is inserted into the cartridge holder, this cartridge holder is attached to the dose setting mechanism. The user uses the dose setting mechanism to select a dose. Before the user injects the set dose, a replaceable double-ended needle assembly is attached to the cartridge housing. This needle assembly may be threaded onto or pushed onto (i.e., snapped onto) a distal end of the cartridge housing. In this manner, a double ended needle mounted on the needle assembly penetrated through a pierceable seal at a distal end of the cartridge. After an injection, the needle assembly is removed and discarded. After the insulin in the cartridge has been exhausted, the user detaches the cartridge housing from the dose setting mechanism. The user can then remove the empty cartridge from the cartridge retainer and replace the empty cartridge with a new (filled) cartridge.

In certain typical a variable dose drug delivery devices such as those described above, a dial sleeve is engaged with the housing of the device via a helical groove. Typically, this dial sleeve is rotated out away from the housing on a helical path to allow the user to set a variable dose of medication. This dial sleeve spins back or rotates back towards the housing when the set dose is delivered.

This helical thread may have one or more radial stop faces that engage when the dial sleeve has been dialed up to a certain non-variable maximum dose. For example, in certain typical drug delivery devices used for the administration of insulin, such a non-variable maximum dose may be on the order of 50-80 International Units (IU). In this manner, a user is prevented from dialing up a dose greater than this non-variable maximum dose. In certain known devices, these stop faces can be molded into the plastic components as fixed stop faces. These stop faces may or may not be part of the helical thread form.

Known dose setting mechanisms that do not allow for varying such a maximum dose setting have certain perceived disadvantages. For example, a drug delivery device having a non-variable maximum dose stop does not enable a user or healthcare professional to limit the maximum dose that can be dialed on a variable dose pen. Therefore, one disadvantage of this arrangement is that it tends to increase the risk of a potential dose error. In addition, such an arrangement makes the device more difficult to set in low light conditions or for users having poor vision.

Another disadvantage of drug delivery devices having a fixed maximum dose is that a parent or a care giver cannot limit the maximum dose that can be delivered from a device. Consequently, such a device may pose certain safety issues when used by a child or elderly patient without supervision.

There is, therefore, a general need for an adjustable maximum dose stop that enables a user or healthcare professional to limit the maximum dose that can be dialed on a variable dose pen. A drug delivery device that utilizes an adjustable maximum dose stop offers a number of advantages. As one example, a user can pre-set the maximum dose of the drug delivery device to be a certain regular daily dose and thereby reduce the risk of a potential dose error. In addition, an adjustable maximum dose stop makes the drug delivery device easier to set in low light conditions or for users having poor vision. For example, with such an arrangement, the user simply dials the dose dial grip until the maximum dose stop engages and then delivers the dose. In addition, such an adjustable maximum dose stop allows a healthcare professional to limit or set the dose for the patient who has poor dexterity, poor vision or limited understanding of variable dose pen types.

There is, therefore, a general need to take these disadvantages associated with issues into consideration in the design and development of drug delivery devices having a non-variable maximum dose stop. Such desired drug delivery devices would allow parents or care givers to set a specific maximum dose that may be set by the drug delivery device and therefore potentially avert an overdose. Such desired devices would also allow patient care givers the opportunity to provide a maximum dose region over which the user can re-adjust the maximum dose.

SUMMARY

According to an exemplary arrangement, a drug delivery device having a variable maximum dose comprises a first tubular member and a second tubular member rotatably coupled to the first tubular member. A maximum stop component is operatively coupled to the first tubular member and the second tubular member. The maximum stop component is movable from a first position to a second position. The first position defines a first maximum dose that may be set by a user of said drug delivery device, and the second position defines a second maximum dose that may be set by the user of the drug delivery device.

According an alternative arrangement; a drug delivery device having a variable maximum dose comprises a housing comprising a helical groove, and a plurality of ratchet teeth. A dial sleeve is coupled to the helical groove and a first stop component engages a first set of the plurality of ratchet teeth. The first stop component is located at a first stop position and defines a first maximum dose of the drug delivery device. The dial sleeve moves the first stop component to a second set of the plurality of the ratchet teeth so that the first stop component moves to a second stop location. The second stop location defines a second maximum dose of the drug delivery device.

In yet another alternative arrangement, a method for providing a drug delivery device having a first and a second maximum dose. The method comprises the steps of:
a. positioning a plurality of ratchet teeth on an inner housing;
b. engaging a first stop component having a plurality of internal features along a set of said plurality of ratchet teeth of said inner housing;
c. positioning a number sleeve in a first position so that said plurality of ratchet teeth of said inner housing engage a first set of said plurality of said internal features of said first stop component defining said first maximum dose, and said number sleeve preventing said inner housing plurality of ratchet teeth from disengaging said plurality of internal feature of said first stop component;
d. displacing said number setting sleeve in a second position so that said number sleeve no longer prevents said disengagement;
e. manipulating said number sleeve so as to select a second maximum dose.

These as well as other advantages of various aspects of the present invention will become apparent to those of ordinary skill in the art by reading the following detailed description, with appropriate reference to the accompanying drawings.

BRIEF DESCRIPTION OF THE DRAWINGS

Exemplary embodiments are described herein with reference to the drawings, in which.

DETAILED DESCRIPTION

Figure 1:
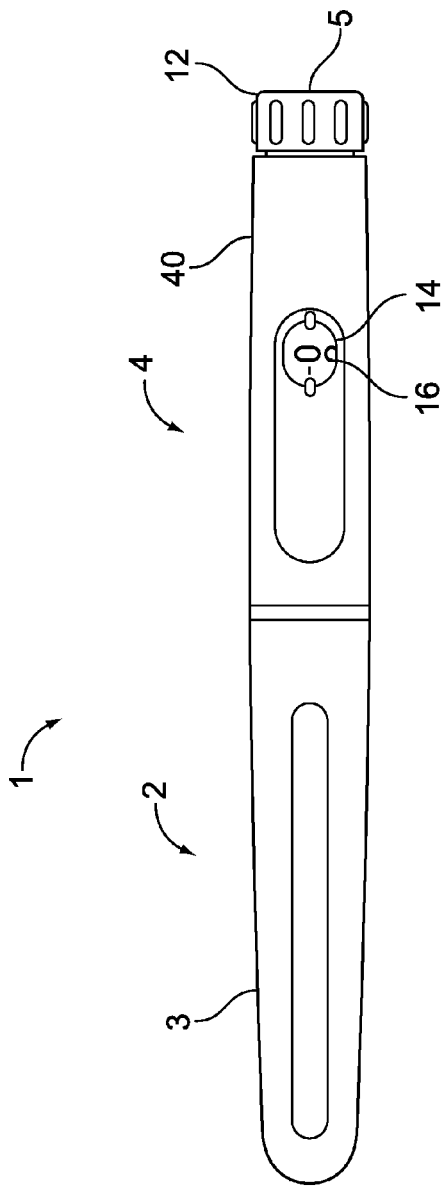
FIG. 1 illustrates a first embodiment of a resettable drug delivery device.

Referring to FIG. 1, there is shown a drug delivery device 1 in accordance with a first arrangement of the present invention. The drug delivery device 1 comprises a housing having a first cartridge retaining part 2, and dose setting mechanism 4. A first end of the cartridge retaining means 2 and a second end of the dose setting mechanism 4 are secured together by retaining features. In this illustrated arrangement, the cartridge retaining means 2 is secured within the second end of the dose setting mechanism 4. A removable cap 3 is releasably retained over a second end or distal end of a cartridge retaining part. As will be described in greater detail, the dose setting mechanism 4 comprises a dose dial grip 12 and a window or lens 14. To set a dose of medication contained within the drug delivery device 1, a user rotates the dose dial grip 12 and the window allows a user to view the dialed dose by way of a dose scale arrangement 16.

Figure 2:
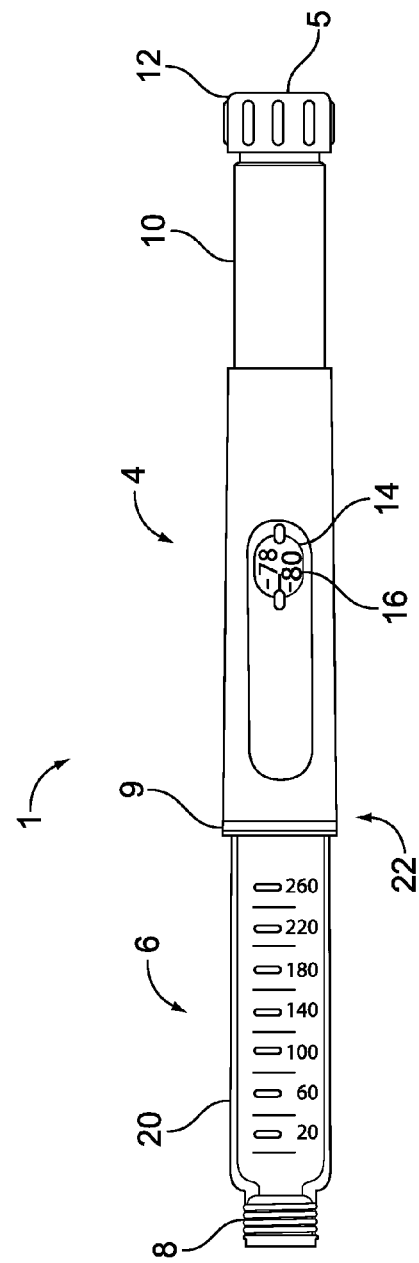
FIG. 2 illustrates a sectional view of the first embodiment of the drug delivery device illustrated in FIG. 1.

FIG. 2 illustrates the medical delivery device 1 of FIG. 1 with the cover 3 removed from the distal end of the medical delivery device. As illustrated, a cartridge 20 from which a number of doses of a medicinal product may be dispensed is provided in the cartridge housing 6. Preferably, the cartridge 20 contains a type of medicament that must be administered often, such as once or more times a day. Once such medicament is insulin. A bung or stopper (not illustrated in FIG. 2) is retained in a first end or a proximal end of the cartridge 20.

The dose setting mechanism 4 of the drug delivery device illustrated in FIG. 2 may be utilized as a reusable (and hence resettable) or a non-reusable (and hence non-resettable) drug delivery device. Where the drug delivery device 1 comprises a reusable drug delivery device, the cartridge is removable from the cartridge housing 6. The cartridge 20 may be removed from the device without destroying the device but merely by the user disconnecting the dose setting mechanism 4 from the cartridge holder 20.

In use, once the removable cap 3 is removed, a user can attach a suitable needle assembly to the distal end of the cartridge holder. Such needle unit may be screwed onto a distal end of the housing or alternatively may be snapped onto this distal end. A replaceable cap 3 is used to cover the cartridge holder 6 extending from the dose setting mechanism 4. Preferably, the outer dimensions of the replaceable cap 3 are similar or identical to the outer dimensions of the dose setting mechanism 4 so as to provide an impression of a unitary whole when the replaceable cap 3 is in position covering the cartridge holder 2.

Figure 3:
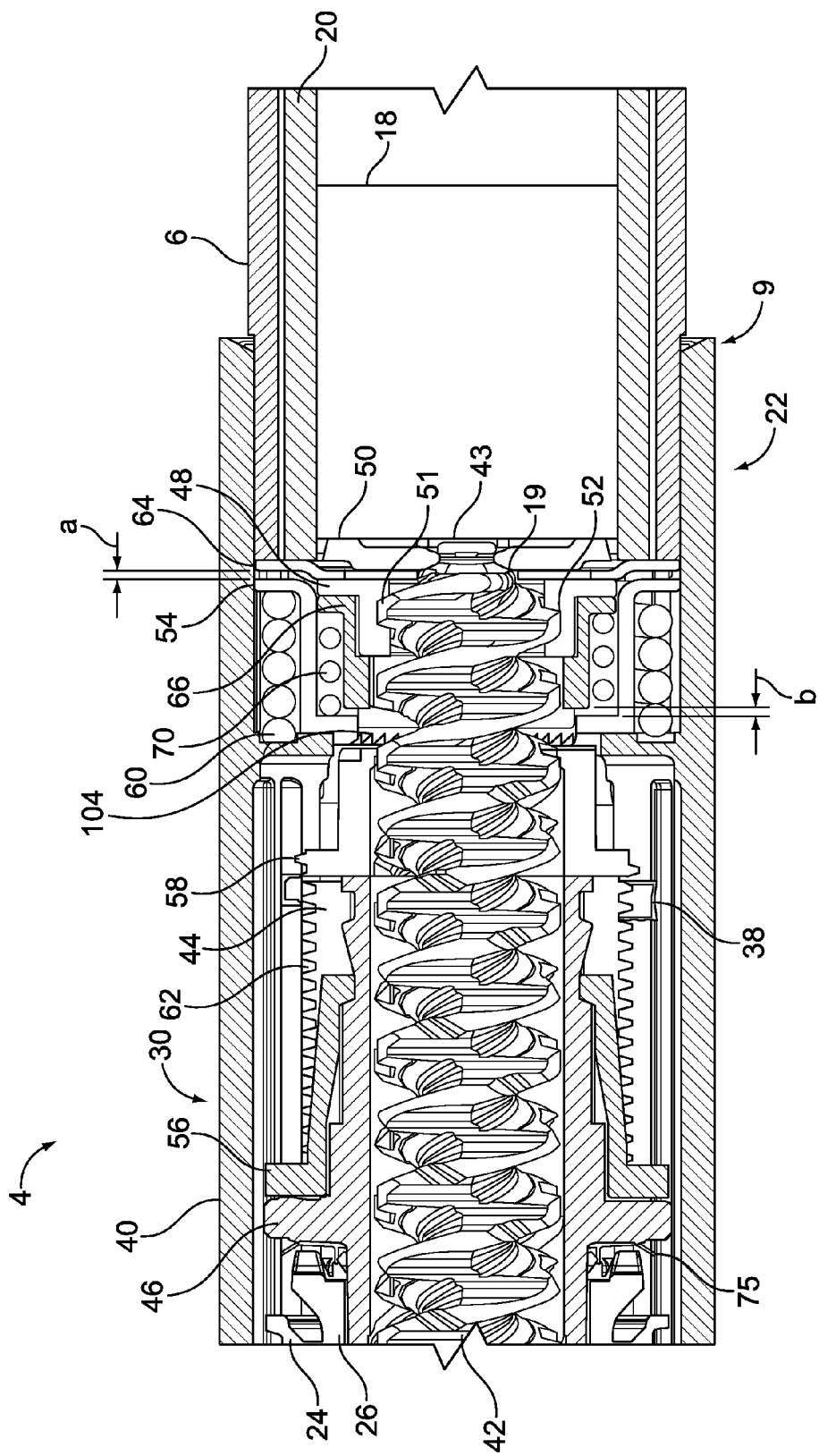
FIG. 3 illustrates a sectional view of the first embodiment of the drug delivery device of FIG. 2 in a first position.

FIG. 3 illustrates a sectional view of the dose setting mechanism 4 removably connected to the cartridge holder 29. The dose setting mechanism 4 comprises an outer housing 40 containing a spindle 42, a number sleeve 24, a clutch 26, and a driver 30. A first helical groove 19 extends from a first end of a spindle 42. In one arrangement, the spindle 42 is of generally circular in cross section however other arrangements may also be used. The first end of the spindle 42 (a distal end 43 of the spindle 42) extends through a pressure plate 64. A spindle bearing 50 is located at the distal end 43 of the spindle 42. The spindle bearing 50 is disposed to abut a second end of the cartridge piston 18. The driver 30 extends about the spindle 42. The clutch 26 is disposed about the driver 30, between the driver 30 and a number sleeve 24. The clutch 26 is located adjacent the second end of the driver 30. A number sleeve 24 is provided outside of the clutch 26 and radially inward of the housing 40. The main housing 4 is provided with a window 14 through which a part of an outer surface 11 of the number sleeve 10 may be viewed.

Returning to FIGS. 1-2, a dose dial grip 12 is disposed about an outer surface of the second end of the number sleeve 10. An outer diameter of the dose dial grip 12 preferably corresponds to the outer diameter of the housing 40. The dose dial grip 12 is secured to the number sleeve 10 to prevent relative movement between these two components. In one preferred arrangement, the dose dial grip and number sleeve 10 comprise a one piece component that is rotationally coupled to a clutch and drive sleeve and axially coupled to the number sleeve 10. However, alternative coupling arrangements may also be used.

Returning to FIGS. 3-5, in this arrangement, driver 30 comprises a first driver portion 44 and a second driver portion 46 and these portions extend about the spindle 42. Both the first and the second driver portions 44, 46 are generally cylindrical. As can be seen from FIG. 6, the first drive portion 44 is provided at a first end with a first radially extending flange 56. A second radially extending flange 58 is provided spaced a distance along the first driver portion 44 from the first flange 56. An intermediate helical groove 62 is provided on an outer part of the first driver portion 44 extending between the first flange 56 and the second flange 58. A portion or a part helical groove 68 extends along an internal surface of the first driver portion 44. The spindle 42 is adapted to work within this part helical groove 68.

A dose limiter 38 (Illustrated in FIG. 3) is located between the driver 30 and the housing 4, disposed between the first flange 56 and the second flange 58. In the illustrated arrangement, the dose limiter 38 comprises a half-nut. The dose limiter 38 has an internal helical groove matching the helical groove 66 of the driver 30. In one preferred arrangement, the outer surface of the dose limiter 38 and an internal surface of the housing 40 are keyed together by way of splines. This prevents relative rotation between the dose limiter 38 and the housing 40 while allowing relative longitudinal movement between these two components.

Referring back to FIGS. 2-5, essentially, in normal use, the operation of the dose setting mechanism 4 occurs as follows. To dial a dose in the arrangement illustrated in FIGS. 1-5, a user rotates the dose dial grip 12. The driver 30, the clutch 26 and the number sleeve 10 rotate along with the dose dial grip 12.

The number sleeve 10 extends in a proximal direction away from the housing 40. In this manner, the driver 30 climbs the spindle 42. At the limit of travel, a radial stop on the number sleeve 10 engages either a first stop or a second stop provided on the housing 40 to prevent further movement. Rotation of the spindle 42 is prevented due to the opposing directions of the overhauled and driven threads on the spindle 42. The dose limiter 38, keyed to the housing 40, is advanced along the thread 66 by the rotation of the driver 30.

FIG. 2 illustrates the medical delivery device after a desired dose of 79 International Units (IU) has been dialed. When this desired dose has been dialed, the user may then dispenses the desired dose of 79 IU by depressing the dial grip 12. As the user depresses the dial grip 12, this displaces the clutch 26 axially with respect to the number sleeve 10, causing the clutch 26 to disengage. However the clutch 26 remains keyed in rotation to the driver 30. The number sleeve 10 and associated dose dial grip 12 is now free to rotate.

The driver 30 is prevented from rotating with respect to the main housing 4 but it is free to move axially with respect thereto. The longitudinal axial movement of the driver 30 causes the spindle 42 to rotate and thereby to advance the piston 18 in the cartridge 20.

In normal use, the first and second portions 44, 46 of the driver 30 are coupled together when the dose dial sleeve 10 is rotated. That is, in normal use, the first and second portions 44, 46 of the driver 30 are coupled together with the dose dial sleeve 10 when a user sets a dose by turning the dose dial grip 12. After each dispensed dose, the spindle 42 is pushed in a distal direction, acting on the bung 18 of the cartridge 20 to continue to expel a dialed dose of medication out of an attached needle assembly releasably connected to the distal end 8 of the cartridge holder 6. After a user uses the drug delivery device 1 to dispense all of the medication contained in the cartridge 20, the user may wish to replace the empty cartridge in the cartridge holder 6 with a new cartridge. The user must then also reset the dose setting mechanism 4: for example, the user must then retract or push the spindle 42 back into the dose setting mechanism 4.

If the user decides to replace an empty cartridge and reset the device 1, the first and second driver portions 44, 46 must be de-coupled from one another. After decoupling the first driver portion 44 from the second driver portion 46, the first driver portion 44 will be free to rotate while the second driver portion 46 will not be free to rotate.

Figure 7:
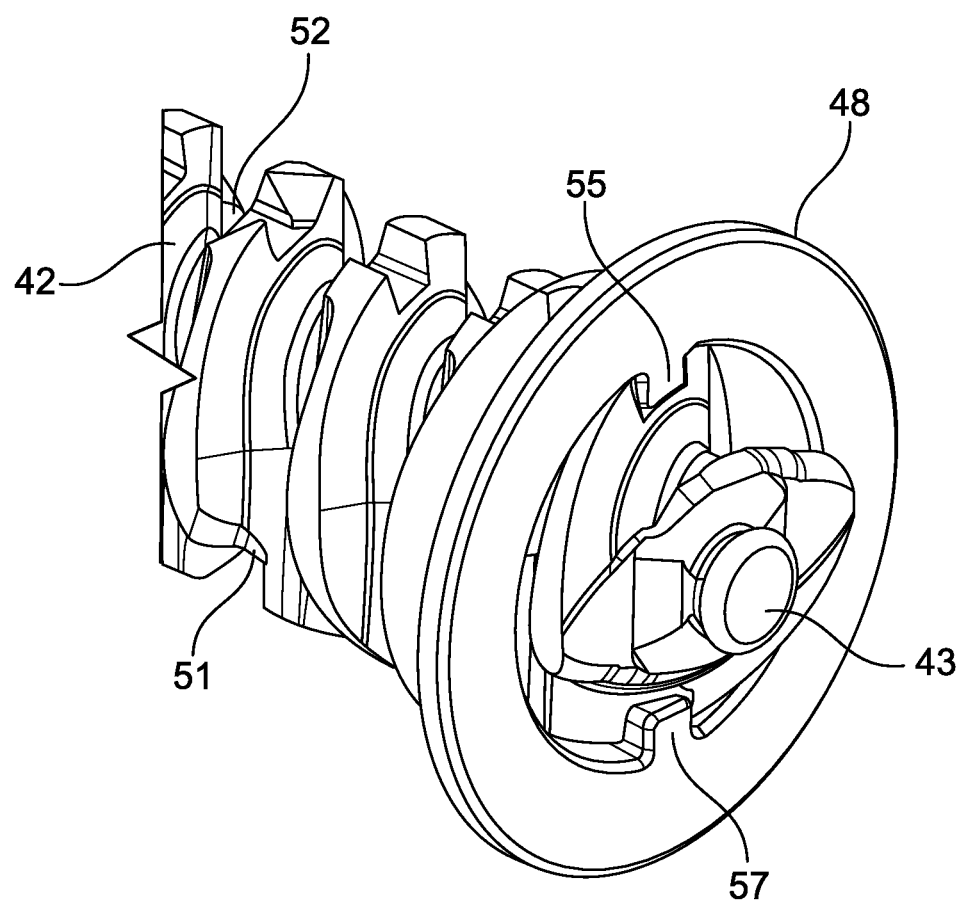
FIG. 7 illustrates a distal end of the spindle of the dose setting mechanism illustrated in FIGS. 2-5.

During a device resetting step, rotating the first driver portion 44 achieves at least two results. First, rotation of the first driver portion 44 will reset the axial position of the spindle 42 with respect to the dose setting mechanism 4 since rotation of the first driver portion 44 causes the spindle 42 to rotate. Rotation of the spindle 42 (because the spindle is splined with the spindle guide 48) moves the spindle in a proximal direction back into the dose setting mechanism. For example, FIG. 7 illustrates one arrangement for connecting the spindle 42 to the spindle guide 48. In FIG. 7, the spindle 42 comprises a first 51 spline and a second spline 52. The spindle guide 48 comprises an essentially circular member having an aperture. The aperture includes two inner protruding members 55, 57 that engage the first and second splines 51, 52 respectively, so that the spindle guide 48 locks onto the spindle and rotates along with the spindle during spindle rotation.

Second, rotation of the first driver portion 44 will also axial move or reset a dose limiter 38 to an initial or start position. That is, as the first driver portion 44 is rotated back to an initial start position, because the dose limiter 38 is threadedly engaged to the outer groove and splined to an inner surface of a housing portion, such as the outer housing 40. In this configuration, the dose limiter 38 is prevented from rotating but will move along the outer groove 62 of the first driver portion 44 as this portion is rotated during a resetting step.

Referring to a first driver arrangement illustrated in FIG. 3, the two portions of the driver 30 are decoupled when the first driver portion 44 is pulled axially away from the second driver portion 46. This may be achieved by the use of a biasing means (such as at least one spring) that interacts together when the cartridge holder 6 is removed from the front or distal end of the device to first lock the relative rotation between the spindle 42 and a spindle guide 48 through which the spindle passes, and then to push this spindle guide 48 and also nut 66 axially a fixed distance. Because the spindle 42 is rotationally locked to the spindle guide 48 and is threadedly engaged with this spindle nut 66, the spindle 42 will move axially.

The spindle 42 is coupled via a groove engaged to the first driver portion 44. The first driver portion 44 is prevented from rotation by a clutched connection to the second driver portion 46. In one preferred arrangement, the second driver portion 46 is prevented from rotation by a clicker detent 75. The clicker detent 75 resides between the clutch and the flange 80 on the drive sleeve 46. Therefore, axial movement of the spindle 42 decouples the two driver portions 44, 46 so that the clutched connection becomes de-coupled.

Figure 4:
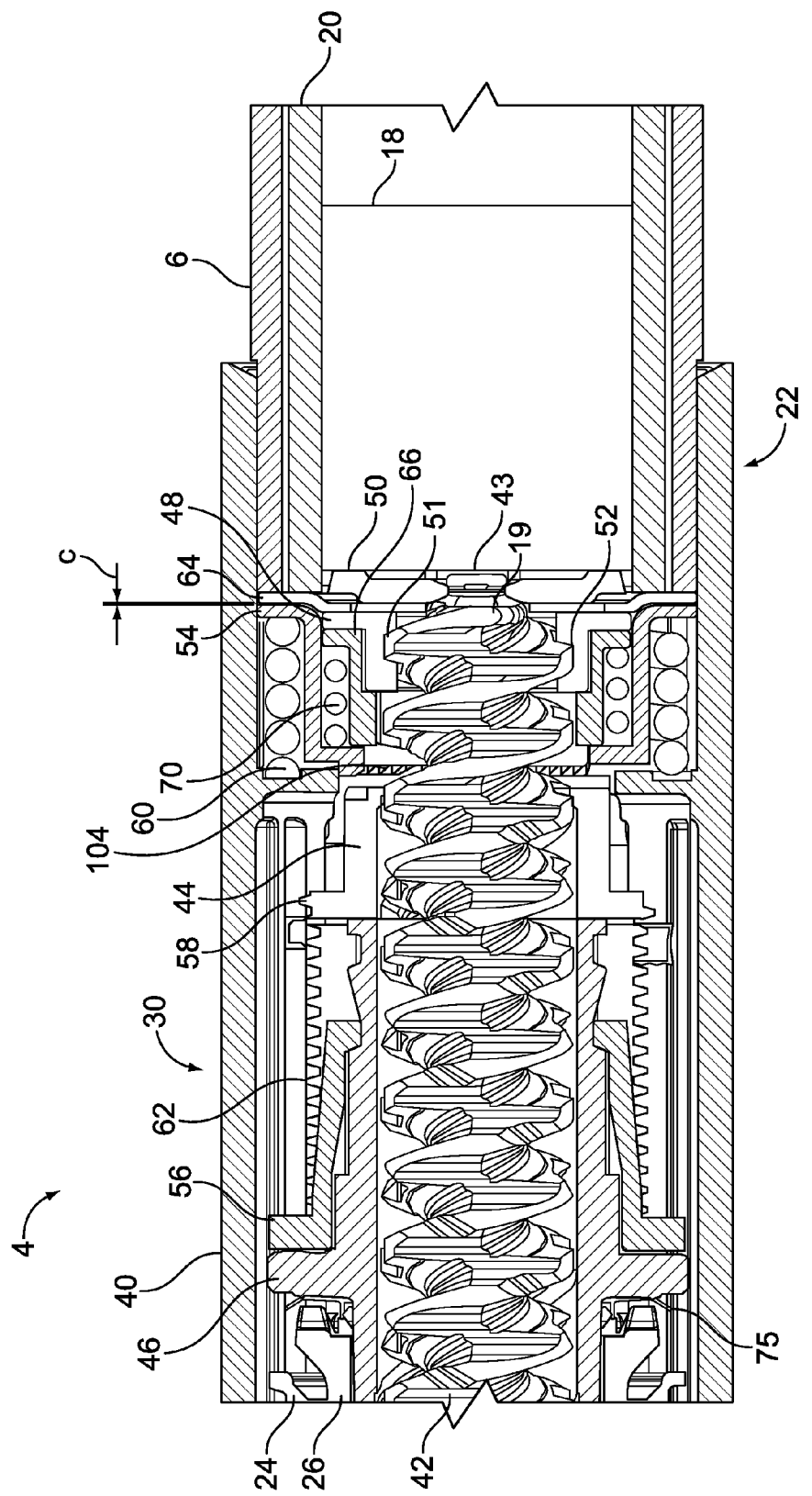
FIG. 4 illustrates a sectional view of the first embodiment of the drug delivery device of FIG. 2 in a second position.
Figure 5:
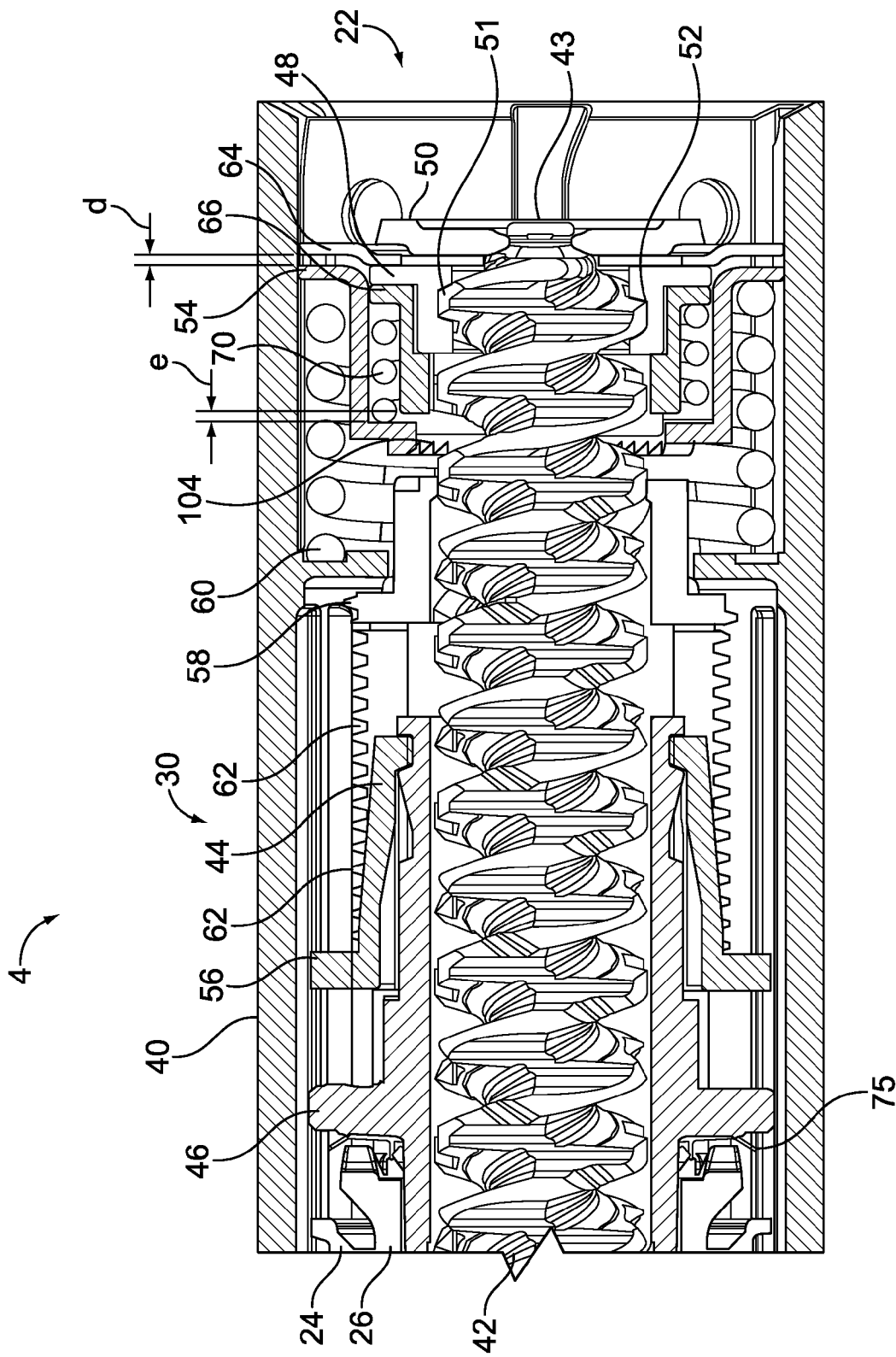
FIG. 5 illustrates a sectional view of the first embodiment of the drug delivery device of FIG. 2 in a third position.

This sequence of operation as the cartridge holder 6 is removed or disconnected from the dose setting mechanism 4 is illustrated in FIGS. 3-5. In FIG. 3, the various component parts of the drug delivery device include: a dose setting housing 40, a cartridge 20, a spindle 42, first driver portion 44; second driver portion 46, spindle bearing 50, spindle guide 48; spring plate 54; a main spring 60, a pressure plate 64, a cartridge holder 20; a spindle nut 66; and a second spring 70. In this preferred arrangement, the spindle guide 54 is rotationally fixed relative to the spindle 20. In addition, the spring plate 54, pressure plate 64 and spindle nut 66 are all rotationally fixed relative to the outer housing.

In FIG. 3, the cartridge holder 6 is fitted via apertures in the pressure plate 64 and applies a load to the spring plate 54. This compresses the first biasing means or main spring 60. These apertures in the pressure plate 64 (not shown) allow the pressure plate 64 to move away from the spring plate 54 (in a distal direction towards the cartridge holder 6) under the action of the second biasing means or second spring 70. This will open up a Gap "A" as shown in FIG. 3. Gap "A" is a gap created between the pressure plate 64 and the spring plate 54. This will also open Gap "B", a gap between the spindle nut 66 and the spring plate 54. This Gap B is illustrated in FIG. 3. The Gap B in conjunction with the light force from the second spring or biasing means 70 moves the spindle nut 66 towards the distal end of the drug delivery device 1. This applies light pressure to the spindle guide 48. The spindle guide 48 is compressed under the action of the second spring 70 between the spindle nut 66 and pressure plate 64. This light force coupled with the friction coefficient on either side of a flange of the spindle guide 48 through which this force acts, provides a resistance to rotation of the spindle guide 48 and therefore a resistance to rotation of spindle 42 as well. One advantage of this configuration is that at the end of a dose, it is advantageous to prevent the spindle 42 from back-winding into the dose setting mechanism 4 under light residual loads that may remain from the cartridge bung 18. By preventing the spindle 42 from back-winding in a proximal direction, a distal end 43 of the spindle 42 (and hence the spindle bearing 50) remains on the bung 18. Maintaining the distal end 43 of the spindle 42 on the bung 18 helps to prevent a user from administrating a potential under-dose.

When the user delivers a dose, as the dispense force increases, the rearward load on the spindle nut 66 increases to a point at which the spindle nut 66 travels back in a proximal direction and compresses the second spring 70. This releases the axial force acting on the spindle guide 48. This removes the resistance to rotation of the spindle guide 48 and hence spindle 42. This configuration therefore prevents back-winding of the spindle 42 under low loads caused by the cartridge bung 18 but does not add to the dispense force once this dispense force has increased above a certain threshold level.

FIG. 4 illustrates the dose setting mechanism 4 of FIG. 3 with the cartridge holder 6 rotated to release a connection type between the housing 40 of dose setting mechanism 4 and the cartridge holder 6. In one arrangement, this connection type 22 is a bayonet connection. However, those of ordinary skill in the art will recognize that other connection types 22 may be used as well such as threads, snap locks, snap fits, luer locks and other similar connection types. In the arrangement illustrated in FIGS. 3-5, by rotating the cartridge holder 6 with respect to housing 40, features that were initially acting on the spring plate 54 to compress the main biasing means 60 through apertures in the pressure plate 64, rotate so that they now release this force created by the main biasing means 60. This allows the spring plate 54 to move in a distal direction until the spring plate 54 contacts the spindle nut 66 on an inside face of the spindle nut 66.

In this second condition, the previous discussed Gap "A" (from FIG. 3) has now been reduced to a Gap "C" (as seen in FIG. 4). In this manner, the relative high axial force from the main biasing means 60 acts through the spring plate 54 to the spindle nut 66 and from the spindle nut 66 through the spindle guide 48 to the pressure plate 64. This relative high axial force from the main biasing means 60 is sufficient to prevent the spindle guide 48, and hence spindle 42, from rotating. After sufficient rotation of the cartridge holder 6, the cartridge holder 6 disengages from the connection type 22 with the housing 40. The cartridge holder 6 is then driven in an axial direction away from the housing 40 by the main biasing means 60 (i.e., in a distal direction). However, during this movement, the main spring 60 continues to load the cartridge holder 6 through the spindle guide 48 and therefore the spindle 42 is prevented from rotation. As the spindle 42 is also threaded to the first driver portion 44, the first driver portion 44 is also pulled axially in a distal direction and in this manner becomes disengaged from the second driver portion 46. The second driver portion 46 is axially fixed and is prevented from rotation. In one arrangement, the second driver portion 46 is prevented from rotation by clicker elements and prevented from axial movement by its axial coupling to the number sleeve.

FIG. 5 illustrates the dose setting mechanism illustrated in FIG. 3 in a third position, that is, with the cartridge holder 6 removed. As the cartridge holder 6 is removed from the housing 40, the bayonet features shown in FIG. 5 (illustrated as round pegs extending radially inwards on inside of inner housing), limit travel of the pressure plate 64 but allows Gap "C" (as shown in FIG. 4) to increase to a wider Gap "D" (as shown in FIG. 5). As a result, Gap "E" develops. Gap "E" removes the high spring force created by the main biasing means 60 from the spindle guide 48. The dose setting mechanism 4 in FIG. 4 is now ready to be rest.

To reset this dose setting mechanism 4, a user retracts the spindle 42 in a proximal direction back into the housing 40 by pushing on the distal end 43 of the spindle 42. Therefore, during this re-setting step of the dose setting mechanism 4, as the spindle 42 is pushed back into the dose setting mechanism 4, the movement of the spindle 42 causes the spindle nut 66 to move back against a light spring force created by the second biasing means 70. This movement releases the axial load and hence resistance to rotation from the spindle guide 48. Therefore, as the dose setting mechanism 4 is reset by the spindle 42 rotating back into the dose setting mechanism 4, the spindle guide 48 also rotates.

As the spindle 42 is pushed back further into the dose setting mechanism 4, the spindle 42 rotates through the spindle nut 66. As the first driver portion 44 is de-coupled from the second driver portion 46, the first driver portion 44 rotates (with the flexible elements 102, 103 running on a conical surface groove 90 formed by the first annular ring 91 on the second half of the dial sleeve 46, FIGS. 5 and 6). This accommodates the axial and rotational movement of the spindle 42.

As the first driver portion 44 rotates during reset, first driver portion 44 also re-sets the dose nut. More specifically, as the first driver portion 44 rotates, the dose nut which is not rotatable since it is splined to an inner surface of the housing 40, traverses along the helical groove 62 provided along an outer surface of the first driver portion 44 and traverses back to an initial or starting position. In one preferred arrangement, this starting position of the dose nut resides along the first radial 56 flange of the first driver portion 44.

After the dose setting mechanism 4 has been reset, the dose setting mechanism 4 must be re-connected to the cartridge holder 6. When re-connecting these two components, the process generally works in reverse. However, this time the axial compression of the main spring 60 causes the first driver portion 44 to re-engage with the second driver portion 46. In this manner, the flexible elements re-engage with the second annular ring 94 on the second driver portion 46.

Figure 6:
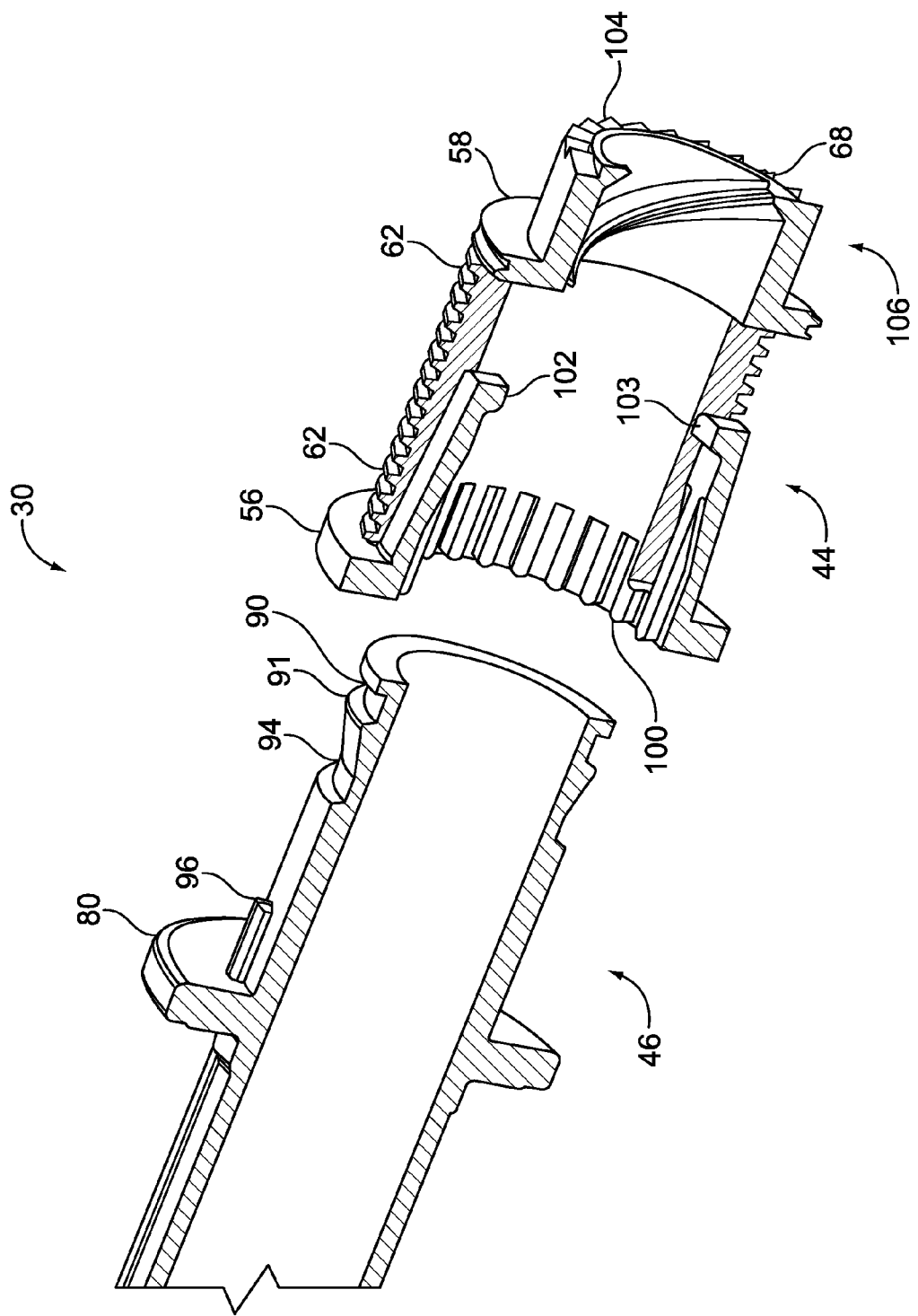
FIG. 6 illustrates a first arrangement of the driver illustrated in FIGS. 2-5 comprising a first driver portion and a second driver portion.

FIG. 6 illustrates a first arrangement of the second driver portion 46 and the first driver portion 44 illustrated in FIG. 3. As shown in FIG. 6, second driver portion 46 is generally tubular in shape and comprises a first annular groove 90 at a distal end of the second driver portion 46. The first annular groove 90 comprises a conical face 91. The second driver portion further comprises a second annular groove 94 and at least one spline 96 positioned along a surface of the second driver portion. The first driver portion 44 is also generally tubular in shape and comprises a first and a second flexible element 102, 103 and a plurality of spline recesses 100. The plurality of recesses 100 releasably connect the longitudinal spline 96 of the first driver portion 44 to second driver portion 46 when both first and second driver portions 44, 46 are pushed axially together so that they releasably engage one another. When pushed together, the flexible elements 102, 103 of the first driver portion 44 are pushed over the first annular groove 90 of the second driver portion 46 and then stop when the flange 80 of the second driver portion abuts the first axial flange 56 of the first driver portion 44.

The first driver portion 44 also includes a plurality of ratchet features 104. These ratchet features 104 are provided at a distal end 106 of the first driver portion 44. These ratchet features 104 engage similar ratchet features on the spring plate 25 which are splined to the housing 2. (See e.g., FIGS. 3-5) At the end of the resetting step, these ratchet features engage one another so as to prevent the first driver portion 44 from rotating thereby ensuring that as the spindle 42 is reset further, the first driver portion moves axially to re-engage the second driver portion 46 rather than rotate on the conical face 90. These features also orientate the spring plate 25 relative to the second driver portion 44 so that the two driver portions 44, 46 engage easily during assembly or after reset. Therefore, these ratchet features also prevent the coupling features 96, 100 from clashing with one another.

Figure 8:
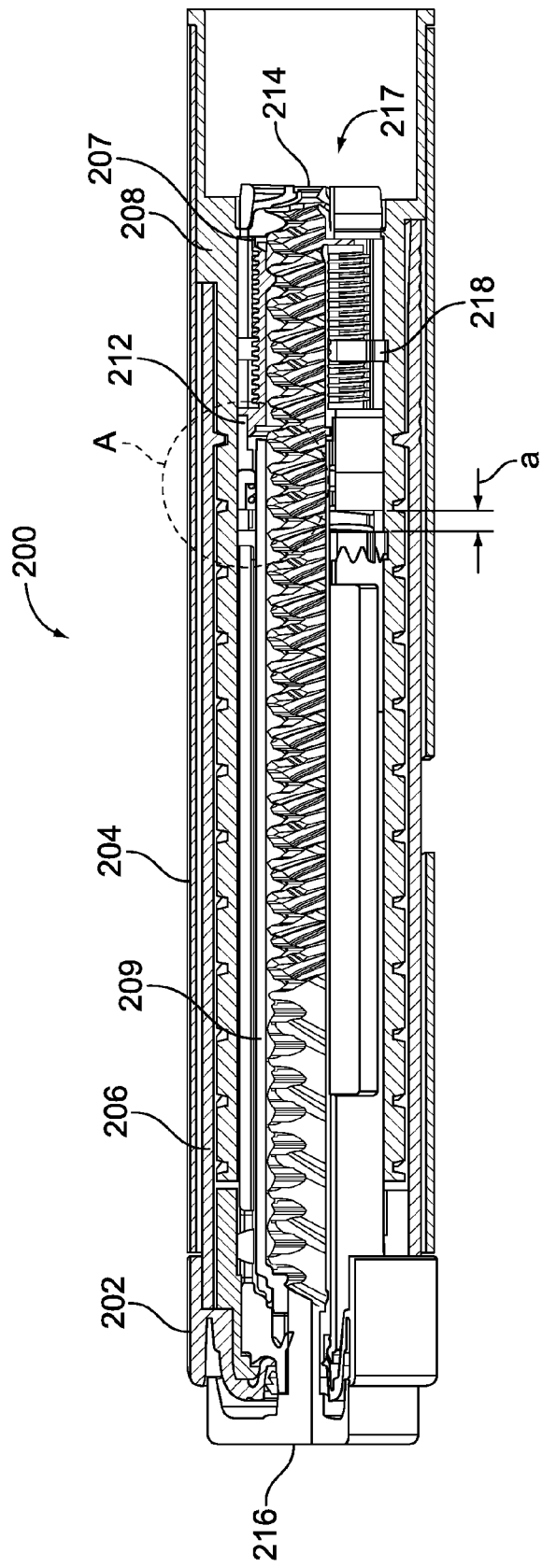
FIG. 8 illustrates a sectional view of a second embodiment of a dose setting mechanism of the drug delivery device illustrated in FIG. 1.
Figure 9:
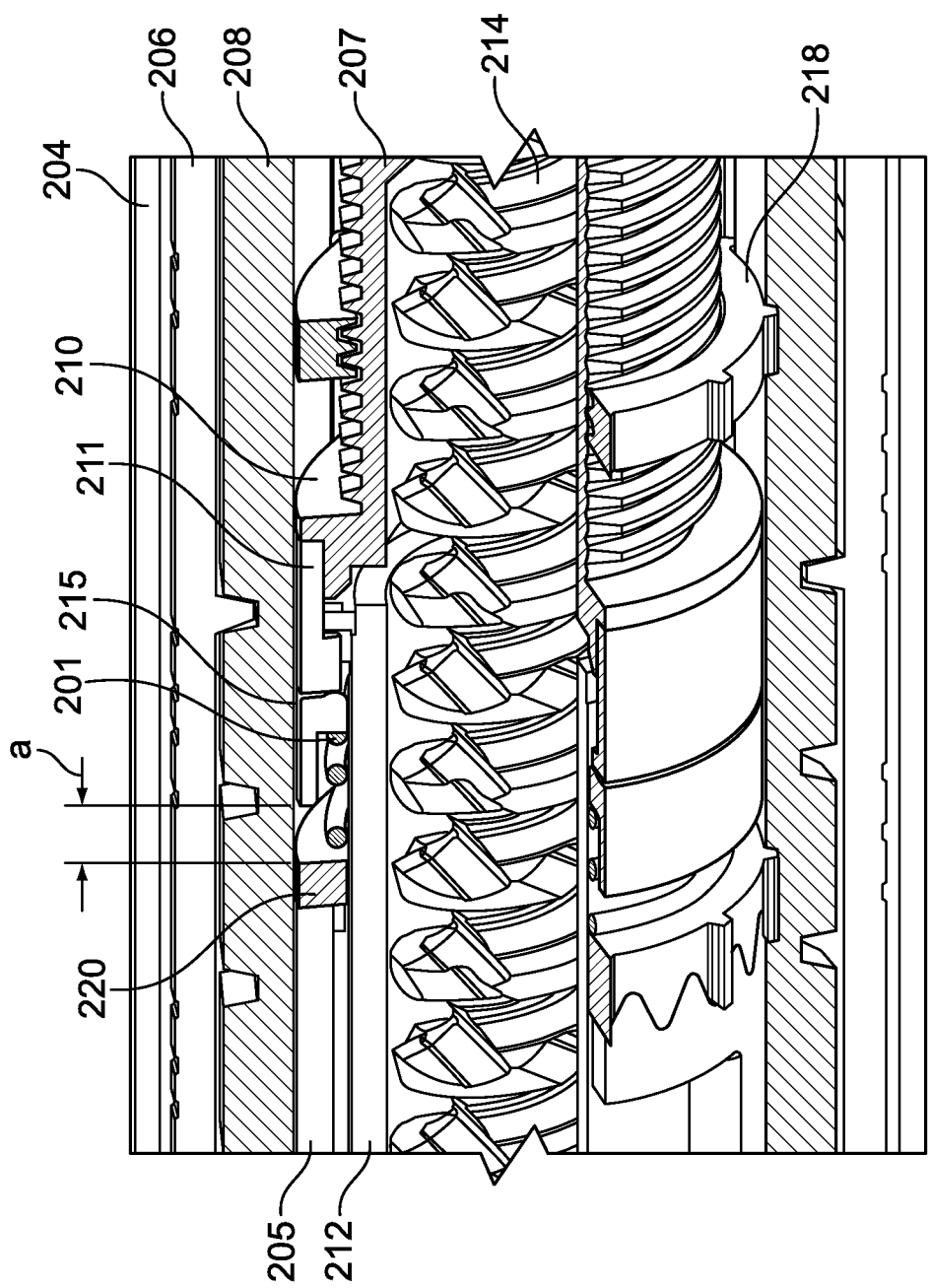
FIG. 9 illustrates a partial sectional view of the second embodiment of the dose setting mechanism illustrated in FIG. 8.
Figure 10:
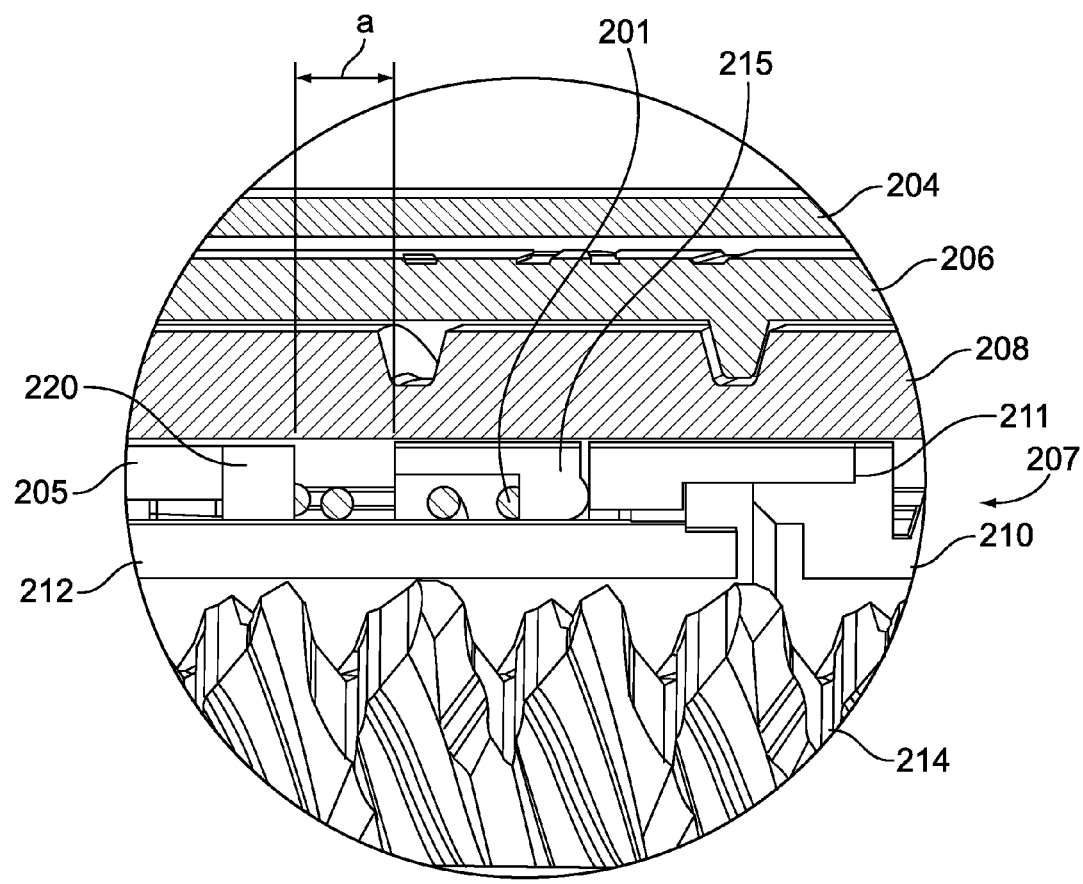
FIG. 10 illustrates a close up view of Gap A illustrated in FIG. 8.

A second arrangement of resettable dose setting mechanism is illustrated in FIGS. 8-10. FIG. 8 illustrates a section view of a second arrangement of a dose setting mechanism 200. Those of skill in the art will recognize that dose setting mechanism 200 may include a connection mechanism for releasably connecting to a cartridge holder, like the cartridge holder 6 illustrated in FIG. 2. However, as those of ordinary skill in the art will recognize, the dose setting mechanism may also include a permanent connection mechanism for permanently connecting to a cartridge holder. FIG. 9 illustrates a portion of the dose setting mechanism illustrating the driver operation. FIG. 10 illustrates a close up view of the coupling between the first driver portion and the second driver portion illustrated in FIG. 9. The second arrangement of the dose setting mechanism 200 operates in generally a similar fashion to the first arrangement of the dose setting mechanism 4 illustrated in FIGS. 1-5.

With reference to FIGS. 8-10, the dose setting mechanism 200 comprises a dose dial grip 202, a spring 201, an outer housing 204, a clutch 205, a driver 209, a number sleeve 206, and an inner housing 208. Similar to the driver 30 illustrated in FIGS. 2-5, driver 209 of dose setting mechanism comprises a first driver portion 207 and a second driver portion 212. In one arrangement, the first driver portion 207 comprises a first component part 210 and a second component part 211. Alternatively, the first driver portion 207 is an integral component part.

Where the dose setting mechanism 200 illustrated in FIGS. 8 and 9 comprises a resettable dose setting mechanism, the driver 209 is de-coupled from the dose setting mechanism 200 when the first driver portion 207 is pushed axially towards the second driver portion 212 (i.e., pushed in a proximal direction). In one arrangement, this may be achieved by pushing axially on a distal end of the spindle 214. This does not require any mechanism associated with removal of a cartridge holder. The mechanism is also designed such that the first and second driver portions 207, 212 and the spindle 214 remain locked together rotationally during dose setting as well as during dose administration.

An axial force on the spindle 214 causes the spindle 214 to rotate due to its threaded connection to the inner housing 204. This rotation and axial movement of the spindle 214 in turn causes the first driver portion 207 to move axially towards the second driver portion 212. This will eventually de-couple the coupling elements 250 between the first driver portion 207 and second driver portion 212. This can be seen from FIG. 11.

This axial movement of the first driver portion 207 towards the second driver portion 212 results in certain advantages. For example, one advantage is that the metal spring 201 will compress and will therefore close the Gap A illustrated in FIGS. 8-10. This in turn prevents the clutch 205 from disengaging from the clicker 220 or from the number sleeve 206. The second driver portion 212 is prevented from rotating since it is splined to the clutch 205. The clicker 220 is splined to the housing 204. Therefore, when the Gap A is reduced or closed up, the second driver portion 212 cannot rotate relative to either the housing 204 or the number sleeve 206. As a consequence, the number sleeve 206 cannot rotate relative to the housing 204. If the number sleeve 206 is prevented from rotating then, as the spindle 214 is retracted back into the dose setting mechanism 200 and thereby re-set, there will be no risk of the number sleeve 206 being pushed out of the proximal side of the dose setting mechanism 200 as a result of a force being applied on the spindle 214.

Similarly, when the drug delivery device is being dispensed, the user applies an axial load to a dose button 216. The dose button 216 is axially coupled to the clutch 205 and this prevents relative axial movement. Therefore, the clutch 205 moves axially towards the cartridge end or the distal end of the dose setting mechanism 200. This movement disengages the clutch 205 from the number sleeve 206, allowing for relative rotation while closing up the Gap A.

As described above, this prevents the clutch 205 from rotating relative to the clicker 220 and hence relative to the housing 204. However, in this scenario, it also prevents the coupling between the first driver portion 210 and the second driver portion 212 from becoming disengaged. Therefore, any axial load on the spindle 214 only disengages the first and second driver portions 210, 212 when the dose button 216 is not axially loaded. This, therefore, does not happen during dispense.

With the dose setting mechanism 200, as a user dials a dose with the dose dial grip 202, the metal spring 201 is selected to be strong enough to maintain engagement of both clutched couplings: the clutched coupling between the clutch 205 and the number sleeve 206 and clutched coupling between the first driver portion 207 and second driver portion 212.

Figure 11:
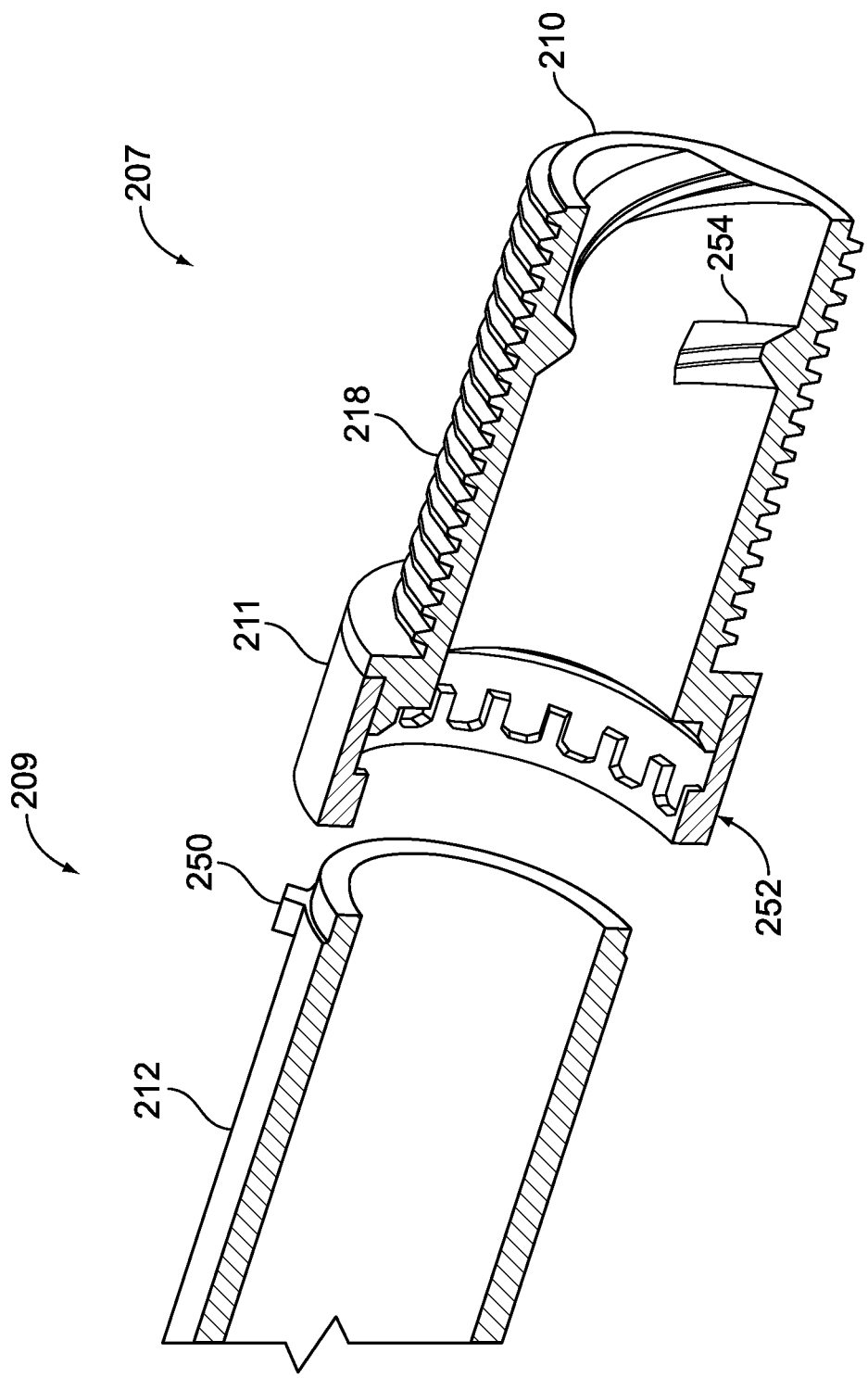
FIG. 11 illustrates a second arrangement of the driver illustrated in FIGS. 8-10 comprising a first driver portion and a second driver portion.

FIG. 11 shows in detail of a first arrangement of the first driver portion 207 and the second driver portion 212 illustrated in FIG. 8. As illustrated in FIG. 11, the second driver portion 212 is generally tubular in shape and comprises at least one drive dog 250 located at a distal end of the second driver portion 212. The first driver portion 207 also has a generally tubular shape and comprises a plurality of recesses 252 sized to engage with the drive dog 250 on the second driver portion 212. The construction of the drive dog and recesses allow disengagement with the drive dog 250 when the first and second driver portions are axially pushed together. This construction also creates a rotational coupling when these components are sprung apart. A dose limiter could be provided on first driver portion 207 and operate similarly to the dose limiter 38 illustrated in FIG. 3.

In this arrangement, the first driver portion 207 comprises a first portion 211 that is permanently clipped to a second portion 210. In this arrangement, the first portion 211 comprises the drive dogs 252 and the second component 210 includes the outer groove for the last dose nut as well as an internal groove 254. This internal groove 254 is used to connect to the spindle 214 and drives the spindle 214 during dose administration.

In the illustrated arrangement, the internal groove 254 comprises a part helical groove rather than a complete helical groove. One advantage of this arrangement is that it is generally easier to manufacture.

As may be seen from the arrangement illustrated in FIGS. 8-10 there is, in addition, certain feature enhancements over the dose setting mechanism 4 illustrated in FIGS. 3-5. These can be added independently of the ability to re-set the device to replace an empty cartridge with a new cartridge. These enhancements, therefore, are relevant to both a re-settable and non-re-settable dose setting mechanism.

One of the advantages of both arrangements illustrated but perhaps in particular in the arrangement illustrated in FIGS. 8-11 is that the dose setting mechanism 200 has a reduced number of components over other known dose setting mechanisms. In addition, apart from the metal coil spring 201 (see FIGS. 9 and 10), all of these components making up the dose setting mechanism 200 may be injection molded using inexpensive and unsophisticated tooling. As just one example, these components making up the dose setting mechanism 200 may be injection molded without the expense and sophistication of a rotating core.

Another advantage of a dose setting mechanism 200 comprising an inner housing 208 such as that illustrated in FIGS. 8-11 is that the dose setting mechanism 200 can be designed, with a slight modification, as a drug delivery device platform that is now capable of supporting both re-settable and non-resettable drug delivery devices. As just one example, to modify the re-settable dose setting mechanism 200 variant illustrated in FIGS. 8-11 into a non-resettable drug delivery device, the first driver portion 211 and 210 and the second driver portion 212 can be molded as one unitary part. This reduces the total number of drug delivery device components by two. Otherwise, the drug delivery device illustrated in FIGS. 8-11 could remain unchanged.

The illustration in FIGS. 8-11 shows an inner housing 208 having a length "L" 230 generally similar in overall length to the dose setting mechanism 200. As will be described, providing the inner housing 208 with a length of "L" has a number of advantages over other known dose setting mechanisms that do not utilize an inner body or an inner body having a length generally equal to that of the length of a dose setting mechanism.

The inner housing 208 comprises a groove 232 provided along an external surface 234 of the inner housing. A groove guide 236 provided on an inner surface 238 of the number sleeve 206 is rotatably engaged with this groove 232.

One advantage of this dose setting mechanism 200 utilizing the inner housing 208 is that the inner housing 208 can be made from an engineering plastic that minimizes friction relative to the number sleeve 206 groove guide 236 and the groove 232. For example, one such an engineering plastic could comprise Acetal. However, those of ordinary skill in the art will recognize that other comparable engineering plastics having a low coefficient of friction could also be used. Using such an engineering plastic enables the material for the outer housing 204 to be chosen for aesthetic or tactile reasons with no friction related requirements since the outer housing 204 does not engage any moving components during normal use.

The inner housing 208 also enables the number sleeve 206 to be provided with a helical groove on an inner surface 238 of the number sleeve 206, rather than providing such a helical groove on an external surface 240 of the number sleeve 206. Providing such an internal groove results in a number of advantages. For example, this results in the advantage of providing more surface area along the outer surface 240 of number sleeve 206 so as to provide the scale arrangement 242. More number sleeve surface area may be used for drug or device identification purposes. Another advantage of providing the helical groove 236 on the inner surface 238 of the dial sleeve 206 is that this inner groove 236 is now protected from dirt ingress. In other words, it is more difficult for dirt to become logged in this inner groove interface than if the groove were provided along the outer surface 240 of the number sleeve 206. This feature is particularly important for a re-settable drug delivery device which will have to function over a much longer period of time compared to a non-resettable device.

The effective driving diameter (represented by 'D') of the grooved interface between the number sleeve 206 and the inner housing 208 is reduced compared to certain known drug delivery devices for the same outer body diameter. This improves efficiency and enables the drug delivery device to function with a lower pitch (represented by 'P') for this groove and groove guide connection. In other words, as the helix angle of the thread determines whether when pushed axially, the number sleeve will rotate or lock to the inner body wherein this helix angle is proportional to the ratio of P/D.

Figure 13:
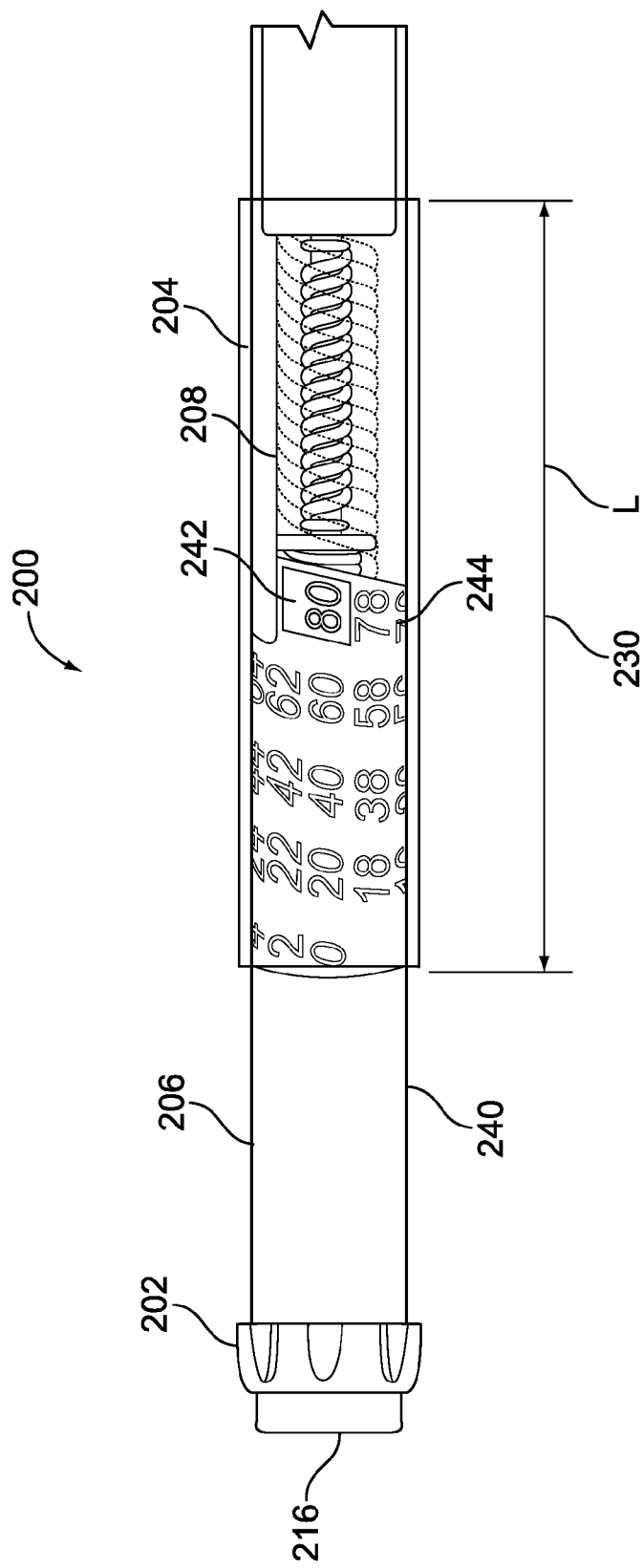
FIG. 13 illustrates the dose setting mechanism illustrated in FIG. 12 in which a user has set a dose.

The number sleeve 206 can be made the length of the mechanism "L" 230 rather than having to split this length into the space required for the number sleeve 206 and a space required for a clicker and a dose limiter. One advantage of this configuration is that it ensures a good axial engagement between the number sleeve 206 and the outer housing 204. This improves the functionality (and perceived quality) of the dose setting mechanism when a user uses the drug delivery device to dial out a maximum settable dose. FIG. 13 illustrates the dose setting mechanism 200 dialed out to a maximum settable dose of 80 International Units ("IU").

Figure 12:
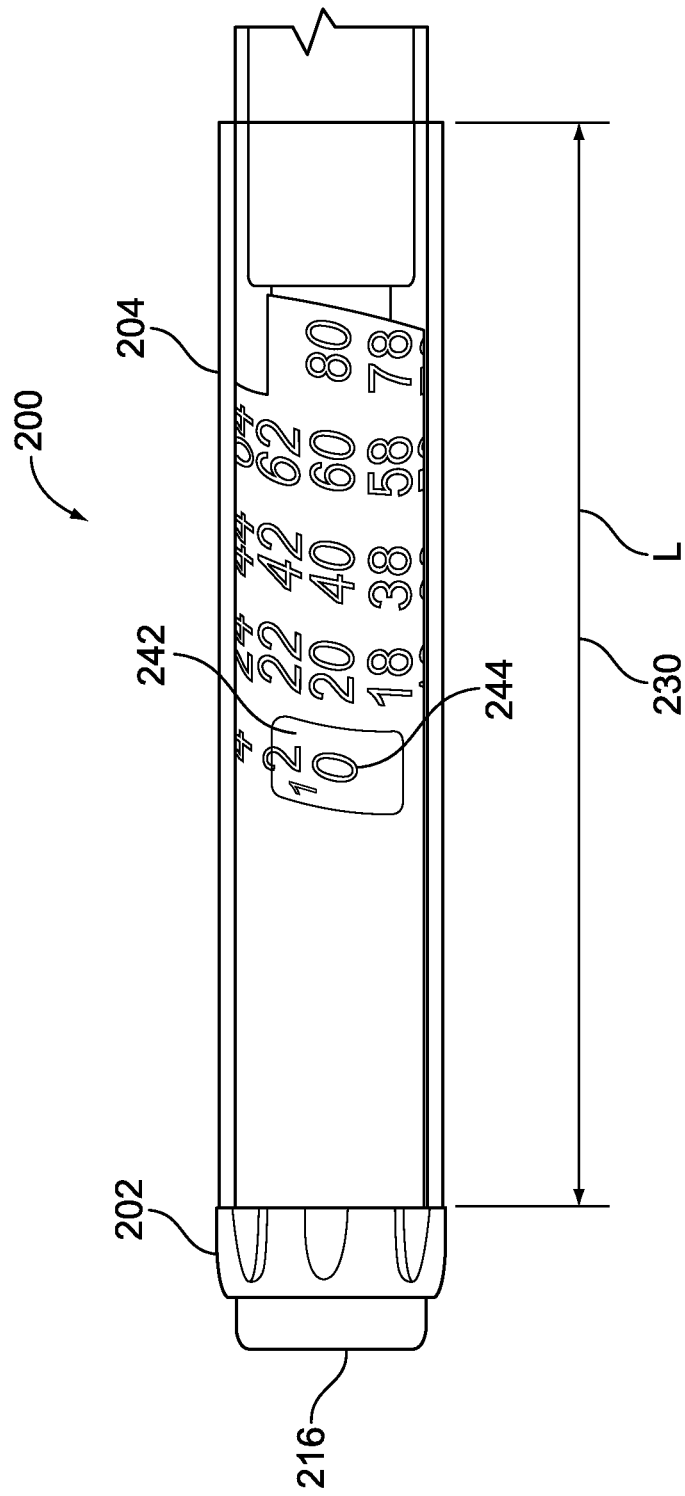
FIG. 12 illustrates the dose setting mechanism illustrated in either FIGS. 2-5 or FIGS. 8-10.

Another advantage is that it enables the scale arrangement 242 to be hidden within the outer housing 204 even when the number sleeve 206 is fully dialed out as may be seen from FIG. 13. However, the design does not limit the position of the window 14 to that shown in FIG. 8 but allows this window 14 to be positioned at near the dose dial grip 202 of the device. However, in arrangements illustrated in FIGS. 12 and 13, the scale arrangement 242 will only be visible by way of the window 14. Also the driver 209 (whether made in two portions or just one unitary component) can be made with a plain internal through hole plus a thread form that can be molded with axially moving core pins. This avoids the disadvantage of a driver having an internal thread with more than one turn and therefore requires a core pin to be rotated out several turns during a de-molding process.

One potential disadvantage of utilizing a dose setting mechanism comprising the inner housing 208 is that the use of the inner housing 208 adds a component part to the overall dose setting mechanism 200. Consequently, this inner housing 208 will tend to increase the overall wall thickness that must be designed to fit between the clutch 205 and number sleeve 206. One way to work around this design issue, as illustrated in FIG. 8, is to reduce the diameter of the clutch 205 and number sleeve 206. This in turn can be achieved because the thread form between the driver 209 and the spindle 214 comprises a male internal feature on the driver 209 and a female external groove form on the spindle 214 that is overlapping with (on a similar diameter with) the spindle groove form that interfaces with the groove along the outer surface 234 of the inner housing 208.

The overlapping of groove forms on the spindle 214 reduces the effective diameter of the thread interface with the driver 209. This also reduces the potential outer diameter of the driver 209 enabling the addition of the inner housing 208 without increasing the overall outer diameter of the dose setting mechanism 200. Another added benefit of the reduced effective diameter of the thread interface with the driver 209 is that it improves efficiency of the drug delivery device during dispense, as explained above.

The window 244 through which the scale arrangement 242 may be viewed can either be just an aperture in the outer housing 204 or can include a clear lens or window designed to magnify the scale arrangement (i.e., printed or laser marked dose numbers) along a portion of the outer surface 240 on the number sleeve 206. The connection of a cartridge holder into the outer housing 204 can be achieved using either a screw or bayonet type connection. Alternatively, any similarly robust design used in drug delivery devices requiring a largely cylindrical part to be removed and then reattached could also be used.

The dose setting mechanism discussed in the previous figures may be utilized either for a drug delivery device comprising a fixed maximum dose setting feature or an adjustable or variable maximum dose setting feature. In order to design a drug delivery device having a dose setting mechanism that allows for an adjustable or variable maximum dose stop, at least one movable member is required. Preferably, this movable member may be moved from a first position defining a first maximum dose to a second position defining a second maximum dose. In this manner, the value of the maximum dose may be varied or adjusted by changing the position of the movable member relative to the housing.

As described below, a device and device components are described that illustrate a drug delivery device where, if the user pulls axially on the number sleeve and displaces this number sleeve axially when a maximum dose stop component is engaged, then the user is able to adjust the position of the additional part(s) relative to an inner housing. This may be accomplished by rotating the number sleeve in this displaced position to thereby alter the maximum dose stop position. Based on a construction of the ratchet teeth of the device (and as will be described in greater detail below), this may be accomplished by rotating the number sleeve either in the clock-wise or the counter clock-wise.

Figure 14:
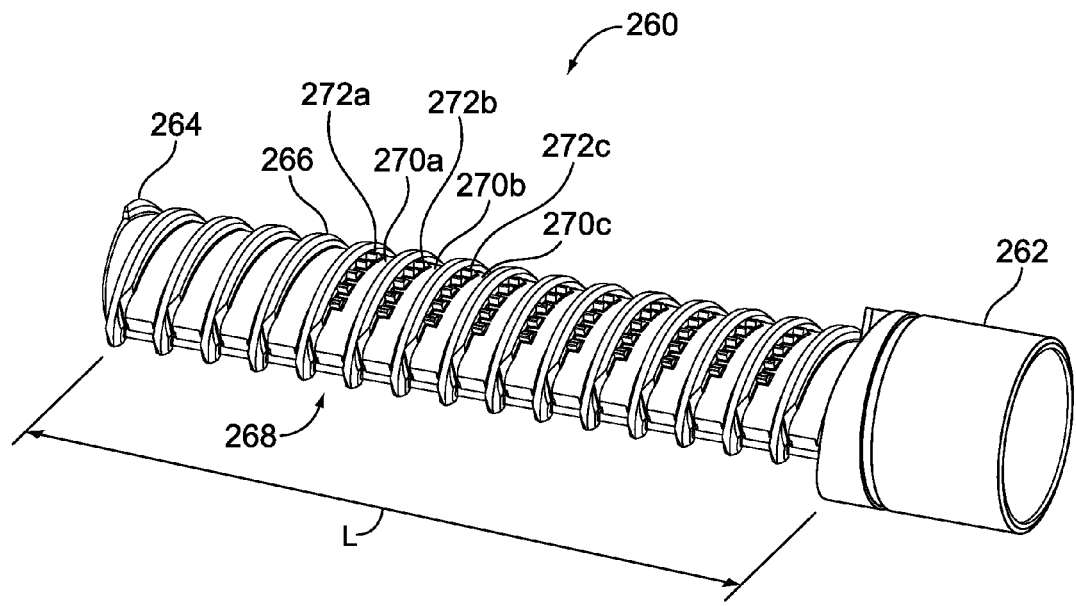
FIG. 14 illustrates one arrangement of an inner housing that may be used with a dose setting mechanism having a variable maximum dose setting feature.

For example, FIG. 14 illustrates one arrangement of an inner housing 260 that may be used with a drug delivery device having a variable maximum dose setting feature. Such an inner housing 260 may have a generally tubular shape and be used with a dose setting mechanism, such as the dose setting mechanism illustrated in FIG. 8. In the arrangement illustrated in FIG. 14, the inner housing 260 comprises a distal end 262 and a proximal end 264. In one preferred arrangement, the inner housing 260 has a length "L" generally similar to the length of the dose setting mechanism, such as the dose setting mechanism illustrated in FIG. 8.

Referring back to FIG. 14, a male guide 266 is provided along an outer surface 268 of the inner housing 260. In a preferred arrangement, this male guide 266 extends along the length "L" of the external surface 268 of the inner housing 260, although other arrangements may also be utilized. In one preferred arrangement, this male guide 266 defines a plurality of grooves (such as grooves 270a, 270b, and 270c) along the outer surface 268 of the inner housing 260. It is the plurality of grooves 270 (a-c) that engage a male guide of the number sleeve, such as the number sleeve 206 illustrated in FIG. 8.

Those of ordinary skill in the art will recognize, however, that these male and female guides can be inter-changed.

Figure 15:
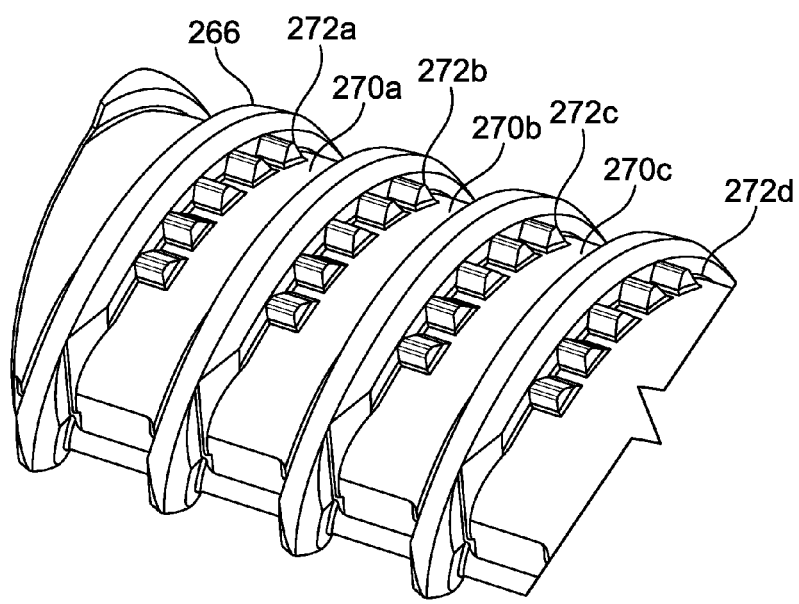
FIG. 15 illustrates one close up view of the inner housing illustrated in FIG. 14.

Preferably, along the outer surface 268 of the inner housing 260 and along a set of the plurality of grooves 270 (a-c), a plurality of ratchet teeth 272 (a-c) are provided. As just one example, FIG. 15 illustrates one close up view of the inner housing 260 illustrated in FIG. 14 where these ratchet teeth are illustrated in greater detail. In the arrangement illustrated in FIG. 15, four sets of a plurality of ratchet teeth 272 (a-d) are provided along a first portion of the inner housing 260. However, those of ordinary skill in the art will recognize, alternative ratchet teeth arrangements could also be used. As just one example, one alternative ratchet teeth arrangement could be provided only near the proximal end 264 of the inner housing 260. As another example, yet another alternative ratchet teeth arrangement could be provided along the entire outer surface of the inner housing 260.

Figure 16:
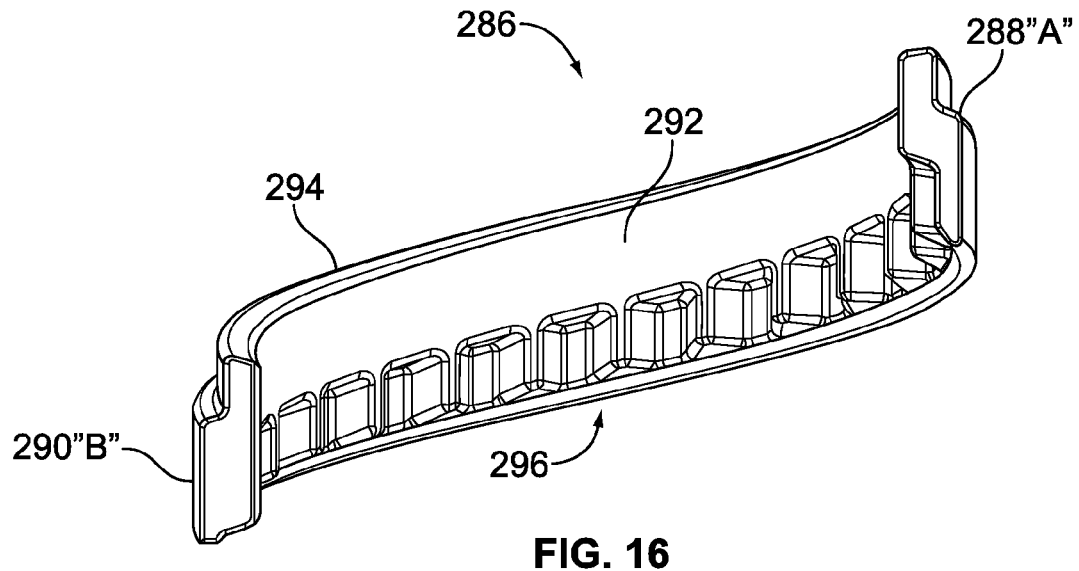
FIG. 16 illustrates one arrangement of a stop component that can be used with the inner housing illustrated in FIG. 14.

FIG. 16 illustrates a stop component 286 that may be used with the inner housing 260 illustrated in FIGS. 14 and 15. The stop component 286 comprises a first maximum dose stop face "A" 288 and a second face "B" 290. As will be described below, the second face "B" 290 may be used for decreasing a maximum stop position of the stop component 286. The stop component 286 further comprises a first or an inner surface 292 and a second or outer surface 294. Preferably, the first or inner surface 292 includes a plurality of internal features 296. In one arrangement, these internal features 296 are shaped to releasably engage a first set 298 of the plurality of the ratchet teeth 272 (a-c) provided along the outer surface 268 of the inner housing 260.

Figure 17:
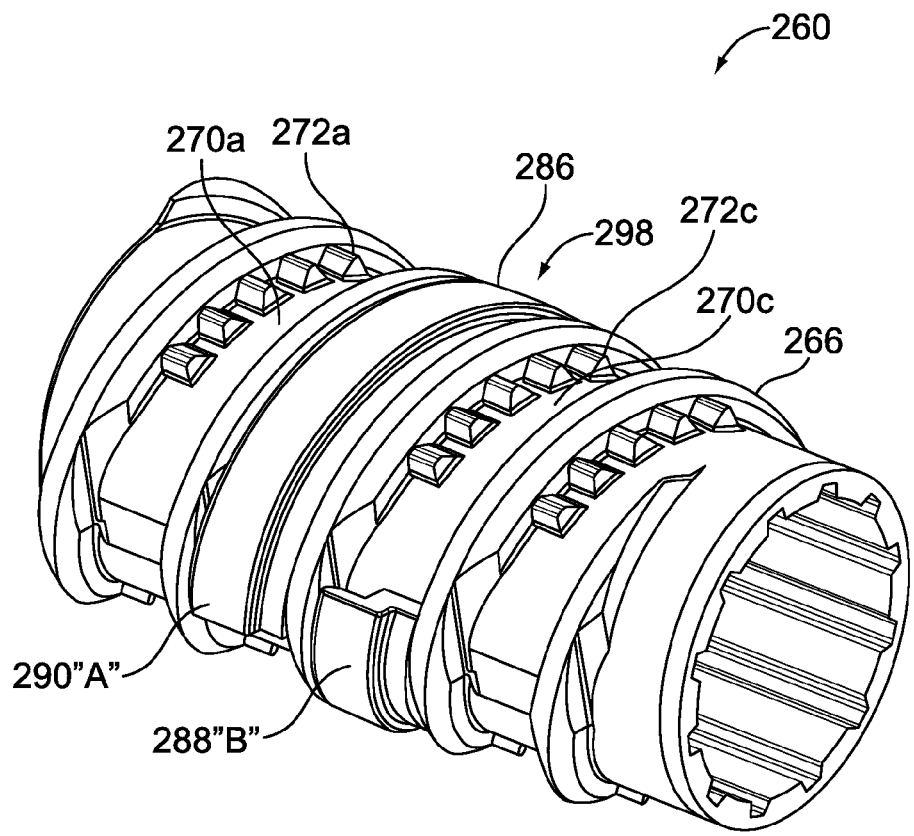
FIG. 17 illustrates the stop component of FIG. 16 releasably engaged to the inner housing illustrated in FIG. 14.

For example, FIG. 17 illustrates the stop component 286 of FIG. 16 releasably engaged in a first maximum stop position 299 along the outer surface 268 of the inner housing 260 illustrated in FIG. 15. Although only one stop component 286 is illustrated in FIG. 17, a second or a third stop component could also be included. One advantage of including two or more stop components along the outer surface 294 of the inner housing 260 is that the overall stop strength of the dose setting mechanism may be increased. As just one example, if the outer surface of the inner housing has a twin start grooves spaced by 180° rotation, then one stop component can be used within each groove.

In one preferred arrangement, the stop component 286 wraps around the outer circumference of the inner housing 260 by more than 180 degrees. This enables the stop component 286 to clip or snap onto the inner housing 260.

Figure 18:
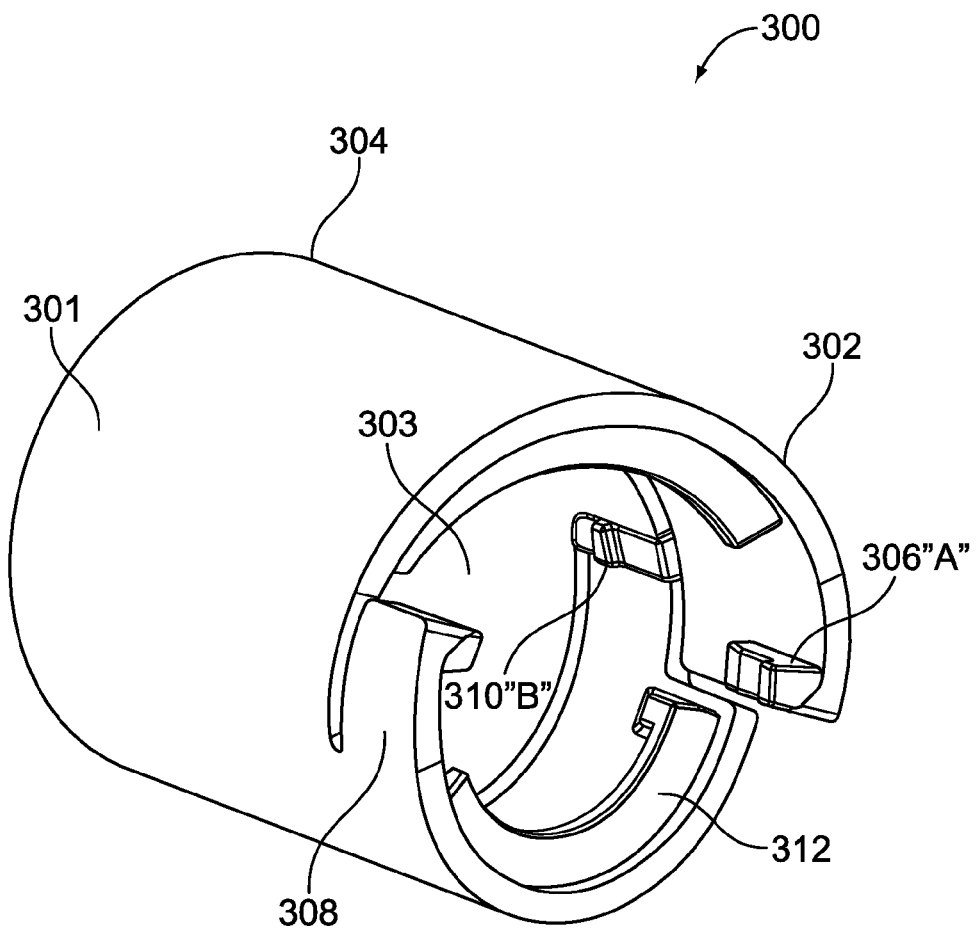
FIG. 18 illustrates a portion of the number or dial sleeve that may be used to releasably engage the inner housing illustrated in FIG. 14.

FIG. 18 illustrates a portion of a number or dial sleeve 300 that may be used to releasably engage the inner housing 260 illustrated in FIG. 14. The number sleeve 300 is generally of a tubular shape and is similar in operation to the number sleeve 206 illustrated in FIG. 8. The dial sleeve 300 comprises a generally smooth outer surface 301 and an inner surface 303. As discussed previously, a scale arrangement may be provided along this generally smooth other surface 301.

The dial sleeve 300 further comprises a proximal end 304 and a distal end 302. Near the distall end 304, the dial sleeve 300 comprises a maximum dose stop face "A" 306. In addition, dial sleeve 300 further comprises a face "B" 310. As will be described below, during a maximum dose setting step, the face "B" 310 engages the second face "B" 290 of the stop component 286 so as to decrease the maximum dose stop position of the stop component 286.

The dial sleeve 300 further comprises a main drive thread 312. This main drive thread 312 engages the groove 274 of the inner housing 260 during a dose setting step and a dose dispense step. A flexible element 308 is also provided near the distal end 304 of the dial sleeve 300.

Figure 19:
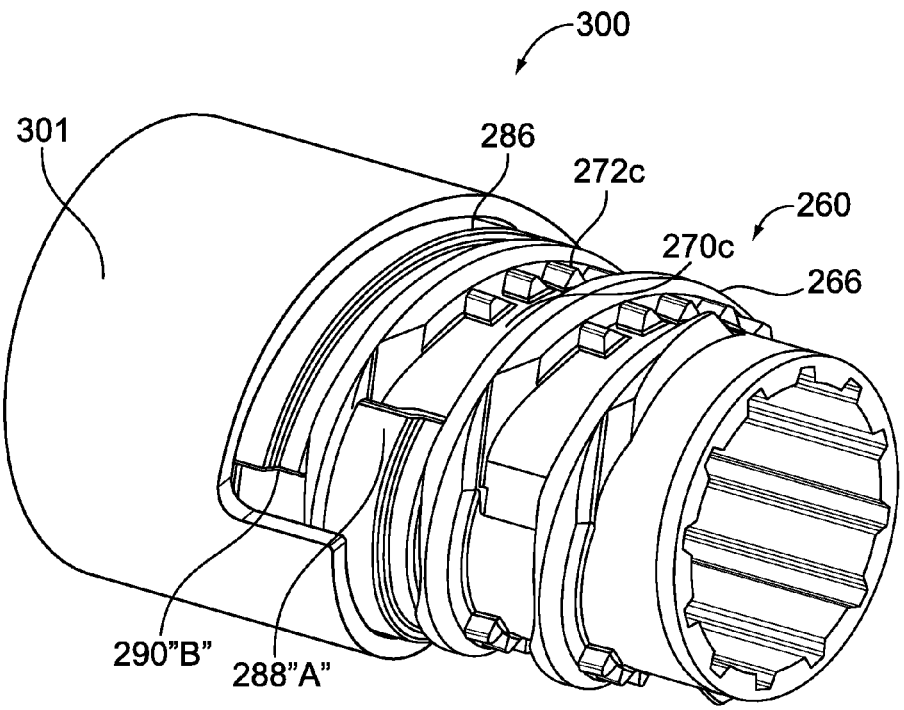
FIG. 19 illustrates the dial sleeve of FIG. 18 engaged to the inner housing of FIG. 14 in a dose setting position.

FIG. 19 illustrates the dial sleeve of FIG. 18 engaged to the inner housing 260 of FIG. 14 in a dose setting position. In this dial sleeve position, the distall end 304 of the dial sleeve 300 is illustrated. The stop component 286 is shown as being prevented from disengaging from the inner housing 260 by the distall end 304 of the dial sleeve 300 because this distal end 304 is overlapping with the stop component 286. In this position, the dose setting mechanism of the drug delivery device may be used to set a dose having a first maximum dose that is defined by the position of the stop component 286 along the groove 270 of the inner housing 260.

In order for this stop component 286 to be moved to a second maximum dose position, the stop component 286 must be allowed to disengage from the inner hosing 260. This may occur by moving or pulling the dial sleeve 260 in a proximal direction so that the distal end 301 of the dial sleeve 300 moves proximally relative to the inner housing 260 and the dial sleeve resides in a second position to define a second maximum dose stop.

Figure 20:
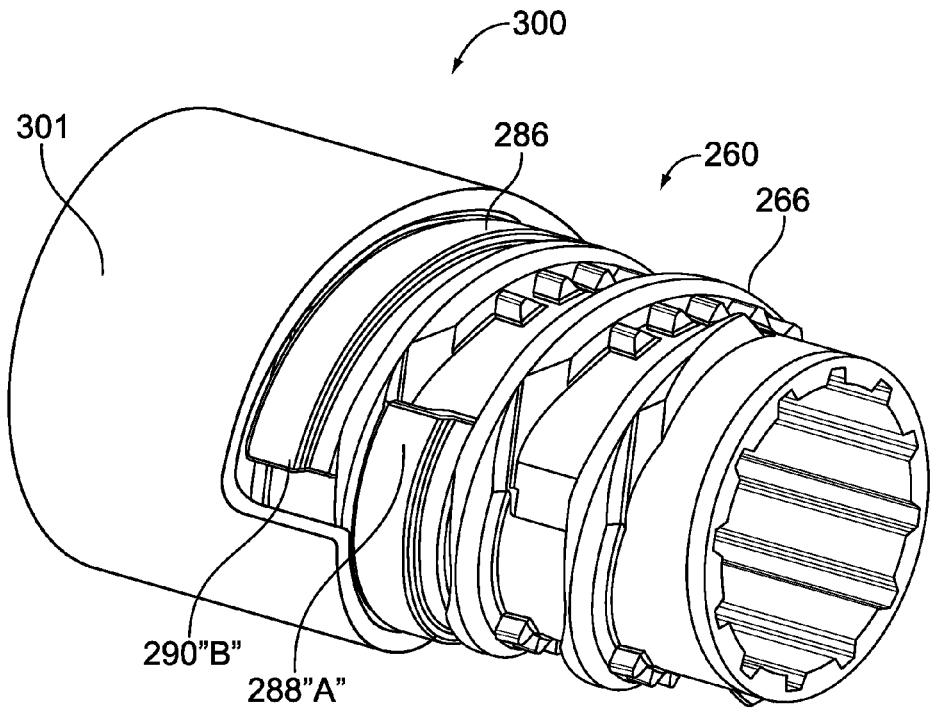
FIG. 20 illustrates the dial sleeve of FIG. 19 in a second position.
Figure 21:
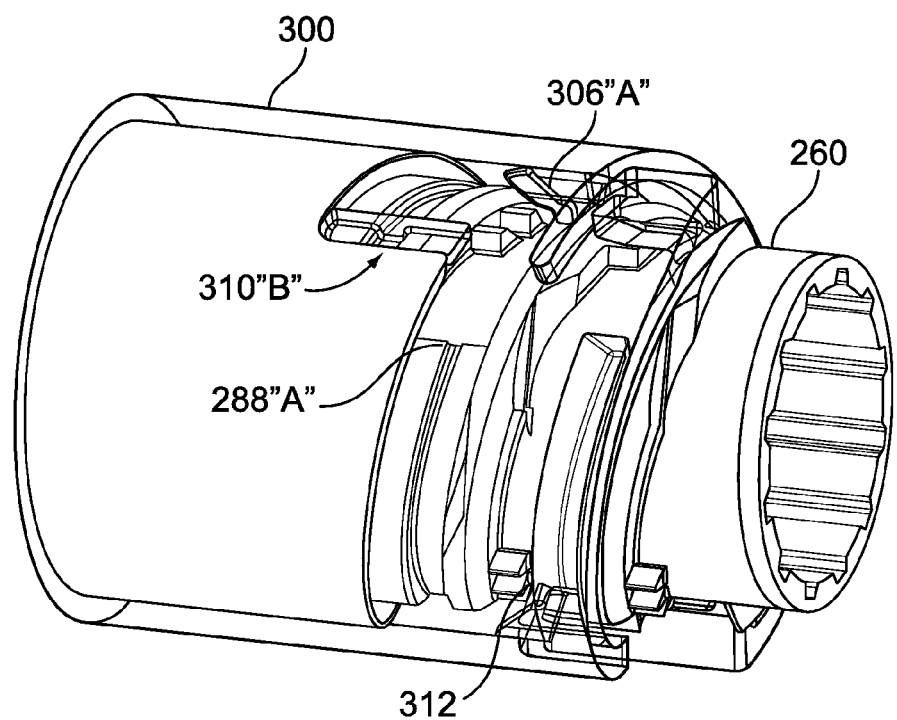
FIG. 21 illustrates the dial sleeve of FIG. 20 in a position prior to engagement of the first maximum stop face of the dial sleeve.
Figure 22:
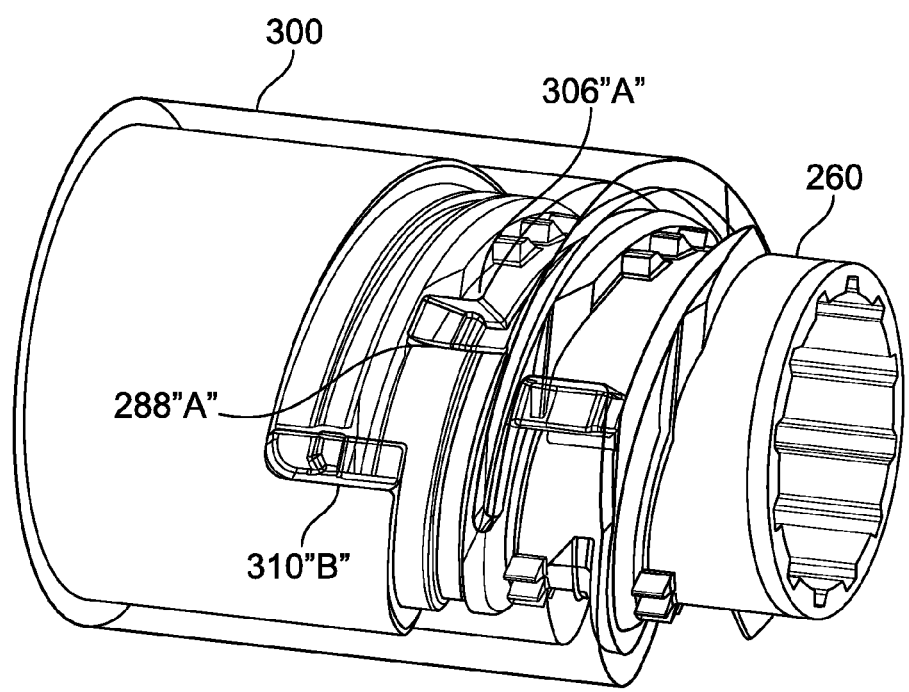
FIG. 22 illustrates the dial sleeve of FIG. 21 once the maximum dose has been dialed.

This second position of the dial sleeve 300 is illustrated in FIG. 20. As can be seen from FIG. 20, the dial sleeve 260 has been moved in a proximal direction. By moving the dial sleeve 300 proximally relative to the inner housing 260, this allows access to the stop component 286 so that it can be rotated to a second position. FIG. 21 illustrates the dial sleeve 300 in a position prior to engagement of the first maximum stop face 288 "A" of the stop component 286 with the "A" maximum dose stop face 306 of the dial sleeve 300. FIG. 22 illustrates the dial sleeve illustrated in FIG. 21 once the maximum dose has been dialed. In this position, the first maximum stop face 288 "A" of the stop component 286 engages the "A" maximum dose stop face 306 of the dial sleeve 300. In other words, FIG. 22 illustrates the position of the dial sleeve 300 with respect to the inner housing 260 when the maximum variable dose has been dialed. If the dial sleeve 300 is pulled in a proximal direction, the second maximum stop face "B" 290 of the stop component 286 engages the face "B" 310 of the dial sleeve 300. The dose setting mechanism is now in a state where the first set maximum dose (i.e., as defined by a first position of the stop component 286 along the inner housing 260) may be changed to a new or second set maximum dose (i.e., as defined by a second position of the stop component 286 along the inner housing 260).

Figure 23:
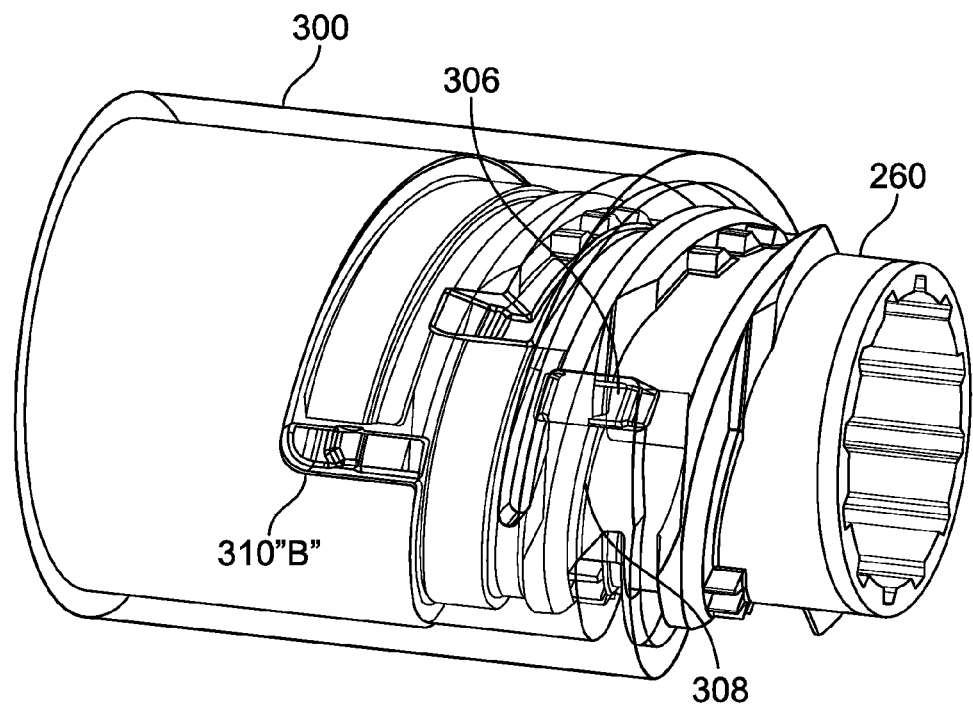
FIG. 23 illustrates a first step of setting a variable maximum dose with the dial sleeve illustrated in FIG. 22.

FIG. 23 illustrates a first step of setting a variable maximum dose with the dial sleeve illustrated in FIG. 22. In FIG. 23, the dial sleeve 300 is pulled back in a proximal direction so as to engage the stop faces "B." Engagement of these stop faces allows rotation of the dial sleeve 300. Depending upon the orientation of the respective ratchet teeth, rotation of the dial sleeve in either the clock-wise or the counter clock-wise direction may increase the variable maximum dose. In this position, rotation of the dial sleeve will also rotate the stop component 286 relative to the inner housing 260. In this proximal position of the dial sleeve 300, the flexible element 308 on the distal end 302 of the dial sleeve 300 interferes with the inner housing 260. This provides a spring like force to counteract the user pulling proximally back on the dial sleeve 300.

Figure 24:
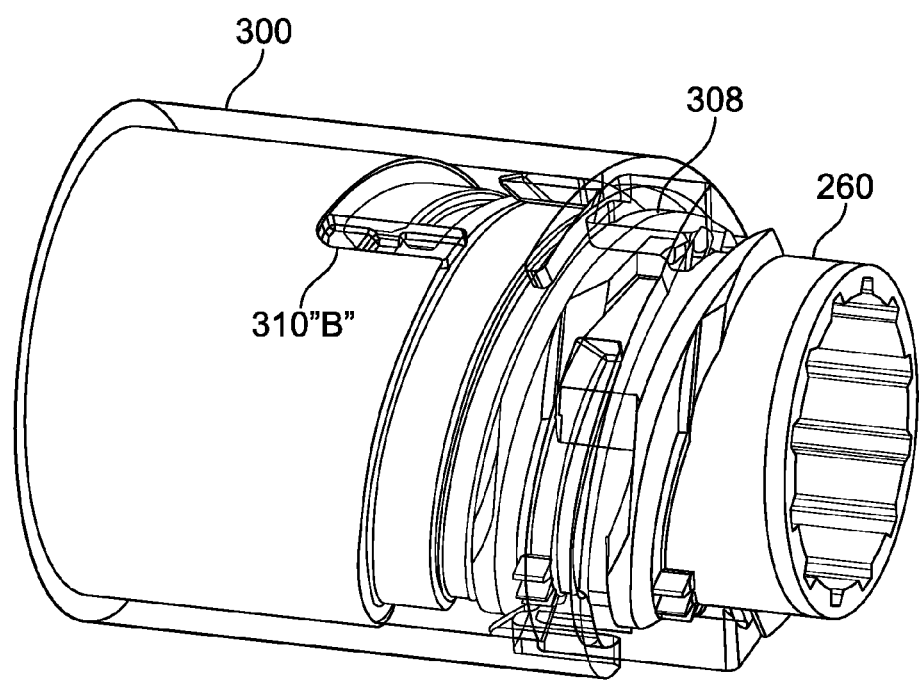
FIG. 24 illustrates the dial sleeve of FIG. 23 after the dial sleeve has been rotated.

FIG. 24 illustrates dial sleeve 300 of FIG. 23 after the dial sleeve has been rotated. As the user rotates the dial sleeve 300 in this pulled back or proximal position, because the inner face 303 of the dial sleeve does not overlap the outer face 294 of the stop component, the dial sleeve 300 may now be rotated to adjust (i.e., rotate) the stop component 286 to a new maximum dose position: a position that either increases or decreases the previously set maximum dose.

During rotation of the dial sleeve 300 and concurrently rotation of the engaged stop component 286, the stop component 286 flexes out radially while bumping over the ratchet teeth 272 (a-c) provided along the outer surface 268 of the inner body 260. Interference of flexible element 308 of the dial sleeve 300 with inner housing 260 is more clearly shown in FIG. 24. Preferably in use, the flexible element 308 flexes radially outwards to relieve interference.

Figure 25:
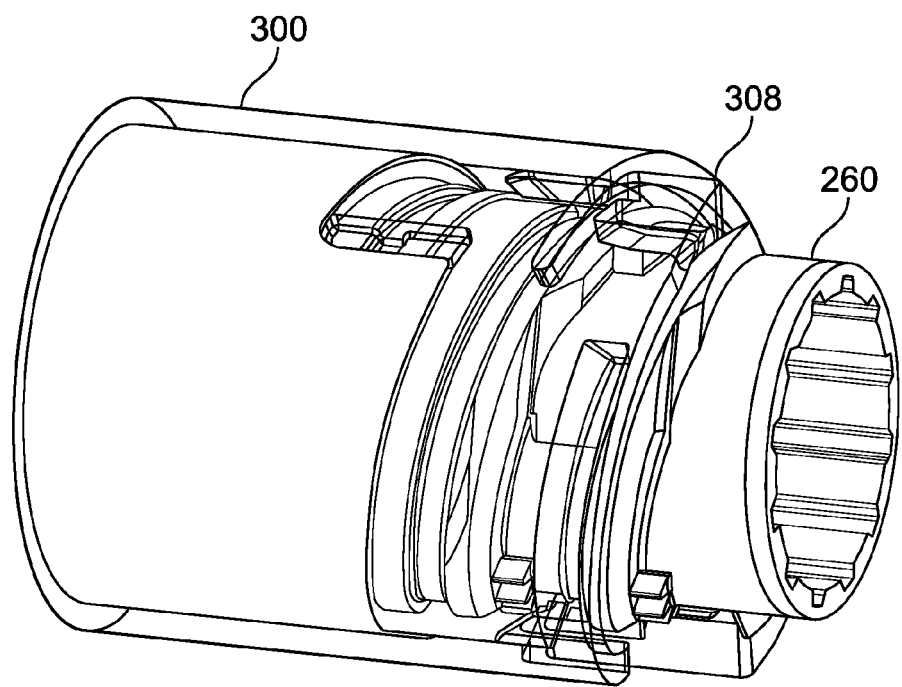
FIG. 25 illustrates a position of the dial sleeve of FIG. 24 after a new maximum dose stop has been set.
Figure 26:
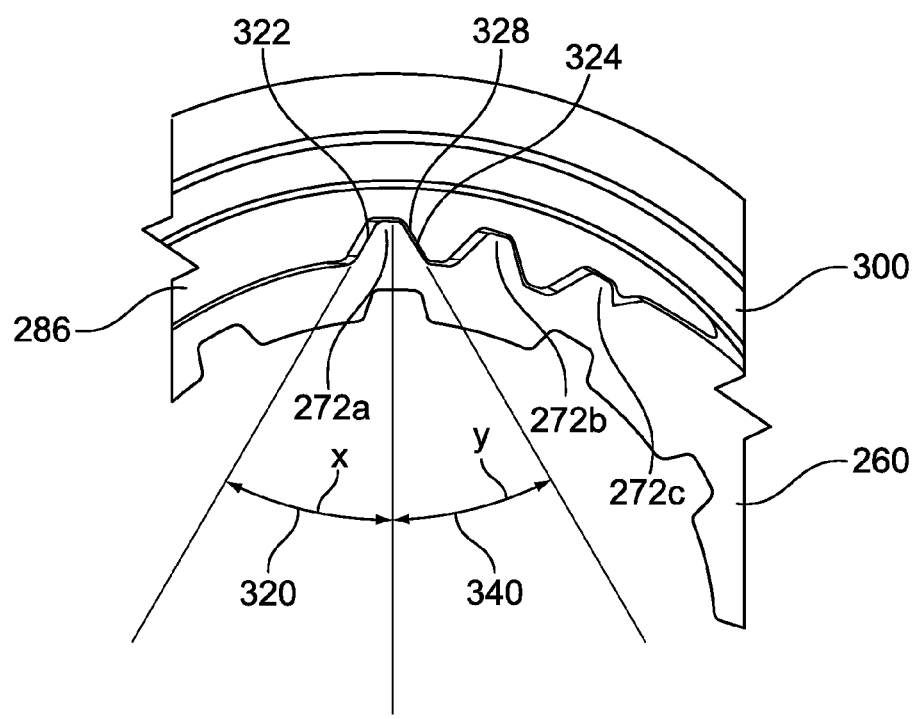
FIG. 26 illustrates a cross-sectional view of the dial sleeve illustrated in FIG. 25.

FIG. 25 illustrates a third position of the dial sleeve 300 illustrated in FIG. 18. In this position, when the user releases the axial force pulling back on the dial sleeve as illustrated in FIG. 24, the flexible elements 308 return the dial sleeve 300 in the distal direction. In this position, the stop component 286 is prevented from rotating since the proximal end of the dial sleeve 300 now overlaps the stop component 286. FIG. 26 illustrates one preferred arrangement of a cross-sectional view of the dial sleeve 300, the stop component 286, and the inner housing 260 illustrated in FIG. 25. As can be seen from FIG. 26, the ratchet teeth 272 (a-c) of the inner housing 260 engage the internal features 296 of the stop component 286. In particular, the ratchet tooth 272(a) comprises a leading edge 322 and a following edge 324. These edges 322, 324 define two angles: angles "X" 320 and angle "Y" 340. In one arrangement, the angles "X" 320 and "Y" 340 can be chosen so that the stop component 286 can be rotated in both directions so as to either increase or decrease the previously set maximum dose as shown.

In one alternative arrangement, angle "Y" 340 can be reduced by modifying the following edge 324 of ratchet tooth 272 (a). This would prevent the stop component 286 from rotating in a certain direction. In this manner, the maximum dose can only be reduced and could not be increased. One advantage of such an arrangement is that the maximum settable dose may not be overridden by a child or other patient. Alternatively, angle "Y" 340 could be reduced by modifying the first leading edge 328 of the stop component 286. Similarly, the follower edge 324 of the ratchet tooth 272 (a) could also be modified. One advantage of this configuration is that if, for example, a maximum dose range of 0-25 UI has been established, the maximum dose would be adjustable up or down within this specific range. However, the stop component 286 could not be rotated so as to set a maximum dose greater than this specified range (i.e., greater than 25 UI), but rather could only be rotated so as to decrease the maximum dose.

One advantage of this arrangement of providing a maximum dose range is that the dose stop also has the option to pre-define a region over which the user can re-adjust the maximum dose. Such an arrangement may be important in reducing risk of an overdose for a child or an elderly patient having limited visibility or limited knowledge of drug delivery device operation.

Alternatively, the ratchet teeth may be configured such that when the dial sleeve w is pulled back, the user can either rotate the dial clockwise or counter-clockwise. Therefore, if the ratchet teeth between the inner housing and the stop component are configured to be symmetric, or rather if the angles X 320 and Y 340 of FIG. 26 are both significantly greater than 0°, then the dial sleeve will increase the maximum dose when it is rotated clockwise and will decrease the maximum dose when rotated anticlockwise. Alternatively, if the angle Y approaches 0° then this will essentially block the adjustment of the stop component in one direction but will allow rotation in the other direction, thereby allowing the user to just to decrease the maximum dose. Exemplary embodiments of the present invention have been described. Those skilled in the art will understand, however, that changes and modifications may be made to these embodiments without departing from the true scope and spirit of the present invention, which is defined by the claims.

The invention claimed is:

1. A drug delivery device having a variable maximum dose, said device comprising:
   a housing, said housing comprising
      a helical groove, and
      a plurality of ratchet teeth;
   a dial sleeve rotatably coupled to said helical groove of said housing, and
   a first stop component engaging a first set of said plurality of ratchet teeth of said housing, said first stop component located at a first stop location along an outer surface of said housing defining a first maximum dose of said drug delivery device;
   wherein said dial sleeve moves said first stop component to a second set of said plurality of said ratchet teeth so that said first stop component moves along said outer surface of said housing to a second stop location, said second stop location defining a second maximum dose of said drug delivery device, and
   wherein said first stop component is user-adjustable (i) from said first stop location to said second stop location and (ii) from said second stop location to said first stop location, such that the variable maximum dose for the drug delivery device can be increased and decreased.

2. The invention of claim 1 wherein rotational movement of said dial sleeve moves said first stop component to said second stop position location.

3. The invention of claim 2 wherein when said dial sleeve is moved to said first position stop location, a first stop face of said dial sleeve engages said maximum dose stop face of said first stop component and thus defines a first maximum dose.

4. The invention of claim 3 further comprising:
   a second stop face of said dial sleeve, said second stop face engages said maximum dose stop position face and moves said first stop component along said inner housing such that said internal features of said first stop component engage a second set of said plurality of ratchet teeth of said inner housing to define a second maximum dose.

5. The invention of claim 1 wherein clockwise rotational movement of said dial sleeve moves said first stop component to said second stop position location.

6. The invention of claim 1 wherein counter clockwise rotational movement of said dial sleeve moves said first stop component to said second stop position location.

7. The invention of claim 1 wherein dial sleeve may be rotated in either a clockwise or a counter-clockwise direction.

8. The invention of claim 1 wherein said stop component comprises a plurality of internal features that releasably engage said first set of said plurality of external ratchet teeth,
   a maximum dose stop face; and
   a maximum dose stop position face.

9. The invention of claim 1 wherein said first maximum dose is greater than said second maximum dose.

10. The invention of claim 1 further comprising a second stop component.

11. The invention of claim 1 wherein said dial sleeve includes a numeric scale, said scale viewable by a user of the drug delivery device and representative of a dose that may be set by said pen type drug delivery device.

12. The invention of claim 1 wherein said first position stop location defines a maximum dose range, said maximum dose range being a pre-defined region over which said user can re-adjust a maximum dose.

* * * * *